(12) United States Patent
Sidorenko et al.

(10) Patent No.: US 11,390,880 B2
(45) Date of Patent: Jul. 19, 2022

(54) COMPOSITIONS AND METHODS FOR EXPRESSING TRANSGENES USING REGULATORY ELEMENTS FROM CHLOROPHYLL BINDING AB GENES

(71) Applicant: CORTEVA AGRISCIENCE LLC, Indianapolis, IN (US)

(72) Inventors: Lyudmila Sidorenko, Johnston, IA (US); Scott Alan Bevan, Indianapolis, IN (US); Cory M Larsen, Zionsville, IN (US); Geny I Anthony, Urbandale, IA (US); Andrew E Robinson, Calvert City, KY (US); Carla N Yerkes, Crawfordsville, IN (US)

(73) Assignee: Corteva Agriscience LLC, Indianapolis, IN (US)

( * ) Notice: Subject to any disclaimer, the term of this patent is extended or adjusted under 35 U.S.C. 154(b) by 0 days.

(21) Appl. No.: 16/641,745

(22) PCT Filed: Aug. 31, 2018

(86) PCT No.: PCT/US2018/049187
§ 371 (c)(1),
(2) Date: Feb. 25, 2020

(87) PCT Pub. No.: WO2019/046776
PCT Pub. Date: Mar. 7, 2019

(65) Prior Publication Data
US 2020/0407742 A1    Dec. 31, 2020

Related U.S. Application Data

(60) Provisional application No. 62/552,692, filed on Aug. 31, 2017.

(51) Int. Cl.
*C12N 15/82* (2006.01)

(52) U.S. Cl.
CPC ..... *C12N 15/8271* (2013.01); *C12N 15/8225* (2013.01); *C12N 15/8274* (2013.01)

(58) Field of Classification Search
None
See application file for complete search history.

(56) References Cited

U.S. PATENT DOCUMENTS

| 2011/0159486 A1* | 6/2011 | Gordon-Kamm | C12N 15/8261 |
| | | | 435/6.1 |
| 2021/0147863 A1* | 5/2021 | Skraly | C07K 14/415 |

FOREIGN PATENT DOCUMENTS

| CN | 101665787 A | 3/2010 |
| WO | 2012125737 A2 | 9/2012 |

(Continued)

OTHER PUBLICATIONS

Walling et al. "Isolation, characterization and evolutionary relatedness of three members from the soybean multigene family encoding chlorophyll a/b binding proteins". Nucleic Acids Research. 16(22) 10477-10492 (Year: 1988).*

(Continued)

*Primary Examiner* — Matthew R Keogh
*Assistant Examiner* — David R Byrnes

(57) ABSTRACT

Provided are compositions and methods for expressing a transgene in plant cells and/or plant tissues using regulatory elements, including the promoters, 5'UTR, 3' UTRs, and/or terminators isolated from *Glycine max* chlorophyll binding Ab genes.

26 Claims, 6 Drawing Sheets

Specification includes a Sequence Listing.

(56) References Cited

FOREIGN PATENT DOCUMENTS

WO     2013005152 A1     1/2013
WO     2016113333 A1     7/2016

OTHER PUBLICATIONS

Nandula, V.K. "Herbicide Resistance Traits in Maize and Soybean:Current Status and Future Outlook". Plants. 8(9):337 (Year: 2019).*
Li, Xinxin, et al., Characterization of soybean [beta]-expansin genes and their expression responses to symbiosis nutrient deficiency, and hormone treatment, Appl Microbiol Biotchnol (2014) 98:2805-2817, Oct. 10, 2013.
EPO, Suppl Search Report Opinion, Oct. 8, 2021.
Genbank Accession X12981.1, Soybean Cab3 gene for PSII LHCII chlorophyll a/b binding protein, NCBI Sep. 5, 1995.
Genbank Accession AC273870.1, *Vigna unguiculata* subsp. *unguiculata* cultivar IT97K-499-35 clone BAC M050108, Jun. 22, 2016.
PCT/US2018/049187 International Search Report dated Dec. 31, 2018.
PCT/US2018/049187 Written Opinion dated Dec. 31, 2018.
PCT/US2018049187 International Preliminary Report on Patentability dated Mar. 3, 2020.
Porto, Milena Silva, et al., Plant Promoters: An Approach of Structure and Function, Mol Biotechnol (2014) 56:38-49.

\* cited by examiner

```
                        SEQUENCE LISTING

<160> NUMBER OF SEQ ID NOS: 28

<210> SEQ ID NO 1
<211> LENGTH: 910
<212> TYPE: DNA
<213> ORGANISM: Glycine max

<400> SEQUENCE: 1
cttcatataa atgtatttca aaagtatttc ttctagaata aactaaagct attacagatg      60
aaaaattctt aaaaaattat ttgaccttca tatatgggtc cttttctaat taataattaa    120
ctatataggt gcattctaaa tgctcctata ttatctgctt tctcctcttc tttccttttt    180
tcctagtcgc tcacgaaaat ctcctataat cctctgcagt tttcgaaatc aataaccgac    240
tcctagaacc tgtccatgtc taacttaata aatcgtgagg gtgtgattgt gattactttg    300
aatctttaat ttttgacatt aaaacaagac caaacaaaaa ccttcaggtt acgtgagact    360
ccaacctacc caagttatgt attagttttt cctggtccag aagaaaagag ccatgcatta    420
gtttattaca actaactata tttcaatttc atgtaagtgt gccccctcat taaaatcgac    480
ctgtgtaacc atcaacctgt agttcgctct tttcaccatt tgtctctctg tctttatctt    540
ccctccccca ttgccaatat ttgttgcaat acaacatctc tccgttgcaa tcactcattt    600
caaattttgt ggttctcatt tgccctagta caacattaga tgtggaccca aaaatatctc    660
acattgaaag catatcagtc acacaattca atcaattttt tccacatcac ctcctaaatt    720
gaataacatg agaaaaaaat agctaagtgc acatacatat ctactggaat cccatagtcc    780
tacgtggaag acccacattg gccacaaaac catacgaaga atctaaccca tttagtggat    840 tatggggtg ccaagtgtac caaacaaaat ctcaaacccc caatgagatt gtagcaatag    900
atagcccaag                                                           910

<210> SEQ ID NO 2
<211> LENGTH: 123
<212> TYPE: DNA
<213> ORGANISM: Glycine max

<400> SEQUENCE: 2
ataagaaccc aaccacttca accccatata aataaacccg gacacaactt caccaagtca     60
ctcaccactt caaaacactc ataacacaaa gcacaaagca aagctcatcc ttgagttaaa    120
aaa                                                                  123

<210> SEQ ID NO 3
```

```
<211> LENGTH: 465
<212> TYPE: DNA
<213> ORGANISM: Glycine max

<400> SEQUENCE: 3
caacttcgtc cccggaaagt gagcgtcaaa gaacgaaatg acttttgaga gttttagat      60
ttgtgtttgg tgaagtactt cagataatgt gaattatctt gtgtatccga atccaactta   120
atgttacttg cttttacaa aactcaagtg tcaatttgtt ctctcatttt atacttctaa    180
gcttttgacg ccacattgaa tttgaactct aattgaacta aaaatgtttt cccttctctc   240
atactaatac taatactaag cagggccact aataatcaca caaaaggaaa gaaacaatat   300
gacaacaaaa ttcgaccatt attatcactg tcatcgaatt ccaatttctt ctcctcacta   360
aaacaggtat gtatatgtaa ttgtaatttc aacatcgtca catgttctta atggagtctg   420
aattttgaag tttgatgctt gctcctgtta aaggatgtt aaaat                    465

<210> SEQ ID NO 4
<211> LENGTH: 556
<212> TYPE: DNA
<213> ORGANISM: Glycine max

<400> SEQUENCE: 4
caacttcgtc cccggaaagt gagcgtcaaa gaacgaaatg acttttgaga gttttagat      60
ttgtgtttgg tgaagtactt cagataatgt gaattatctt gtgtatccga atccaactta   120
atgttacttg cttttacaa aactcaagtg tcaatttgtt ctctcatttt atacttctaa    180
gcttttgacg ccacattgaa tttgaactct aattgaacta aaaatgtttt cccttctctc   240
atactaatac taatactaag cagggccact aataatcaca caaaaggaaa gaaacaatat   300
gacaacaaaa ttcgaccatt attatcactg tcatcgaatt ccaatttctt ctcctcacta   360
aaacaggtat gtatatgtaa ttgtaatttc aacatcgtca catgttctta atggagtctg   420
aattttgaag tttgatgctt gctcctgtta aaggatgtt aaaattagac caaactttat    480
taccagcaat agaatctcat atacgagaaa gtactttggg ttctcccatc ttccttcact   540
ccagtggtag ccagaa                                                   556

<210> SEQ ID NO 5
<211> LENGTH: 1033
<212> TYPE: DNA
<213> ORGANISM: Glycine max

<400> SEQUENCE: 5
cttcatataa atgtatttca aaagtatttc ttctagaata aactaaagct attacagatg      60
aaaaattctt aaaaaattat ttgaccttca tatgtgggtc cttttctaat taataattaa   120
ctatataggt gcattctaaa tgctcctata ttatctgctt tctcctcttc tttcctttt    180
tcctagtcgc tcacgaaaat ctcctataat cctctgcagt tttcgaaatc aataaccgac   240
tcctagaacc tgtccatgtc taacttaata aatcgtgagg gtgtgattgt gattactttg   300
aatctttaat ttttgacatt aaaacaagac caaacaaaaa ccttcaggtt acgtgagact   360
ccaacctacc caagttatgt attagttttt cctggtccag aagaaaagag ccatgcatta   420
gtttattaca actaactata tttcaatttc atgtaagtgt gccccctcat taaaatcgac   480
ctgtgtaacc atcaacctgt agttcgctct tttcaccatt tgtctctctg tctttatctt   540
ccctccccca ttgccaatat ttgttgcaat acaacatctc tccgttgcaa tcactcattt   600
caaatttgt ggttctcatt tgccctagta caacattaga tgtggaccca aaaatatctc   660
```

| | |
|---|---|
| acattgaaag catatcagtc acacaattca atcaatttt tccacatcac ctcctaaatt | 720 |
| gaataacatg agaaaaaaat agctaagtgc acatacatat ctactggaat cccatagtcc | 780 |
| tacgtggaag acccacattg gccacaaaac catacgaaga atctaaccca tttagtggat | 840 |
| tatgggggtg ccaagtgtac caaacaaaat ctcaaacccc caatgagatt gtagcaatag | 900 |
| atagcccaag ataagaaccc aaccacttca accccatata aataaacccg gacacaactt | 960 |
| caccaagtca ctcaccactt caaaacactc ataacacaaa gcacaaagca aagctcatcc | 1020 |
| ttgagttaaa aaa | 1033 |

```
<210> SEQ ID NO 6
<211> LENGTH: 818
<212> TYPE: DNA
<213> ORGANISM: Glycine max

<400> SEQUENCE: 6
```

| | |
|---|---|
| agggggtaca ctttacataa ttgtatttca aaagtatttc ttcaagagta aacaaaagct | 60 |
| agcacagatg aaaaaacatt ttaaaaaaat tatttgacct tcatgtacga gtgctttcta | 120 |
| aattaaataa ttgactgtat agaggtgcct tctaaattct cctatattat ttcagcttgc | 180 |
| tttctttctt attttcccca gtcgctcacg aaaatctcct attctaatat cttgtgcagt | 240 |
| tttggcaatc aacatgtatt agtgagggtg tgactgtgat tactttgatt tttgaaacta | 300 |
| aaacaatacc aaacaaaaac cctctggtaa cgtgaagtaa tagtttttt ggtactgaaa | 360 |
| gaaaaaagat agccatgtat ttatttagtt tattacaact aactatattt caatttgatg | 420 |
| taagtgcccc ctcattaaaa tggacctgtg taaccatcaa cctctagttc gctcttttca | 480 |
| ccatttgtct ctctgtctct gacttggcaa tatttgaaat tttgtggttc tcatttccct | 540 |
| tagtacaaca ccagatgtgg acccaaaaat atctcagaca ttgaaactaa ggatagccac | 600 |
| ataattcaag ccattttcca cgtcacctcc tcaatggaat agcataagaa aataagttaa | 660 |
| caaacatatc tactggaatc ccatagtcct acgtggaaga cccacattgg tcagaaaagc | 720 |
| agagaaagaa tctaacccat ttagtggatt atagggggtgc caagtgtacc aaacaaaatc | 780 |
| tgaaagcccc aatgagatag tagcaataga taggccaa | 818 |

```
<210> SEQ ID NO 7
<211> LENGTH: 115
<212> TYPE: DNA
<213> ORGANISM: Glycine max

<400> SEQUENCE: 7
```

| | |
|---|---|
| gataagaacc ccaaccactt gaagcccata taaataaacc cccacacaac ttcactgaat | 60 |
| cactcacaac tccataacac aaggcagaaa gcaagctcat cctagagttt taaaa | 115 |

```
<210> SEQ ID NO 8
<211> LENGTH: 296
<212> TYPE: DNA
<213> ORGANISM: Glycine max

<400> SEQUENCE: 8
```

| | |
|---|---|
| gcatgaaaga aaaggatgac ttgtggactt ttgagagttt ttagatttgt gtttggtgaa | 60 |
| gtatatgtta ttgcaatgta cttcagataa tgtgaattat cttgtgtatc cgaatccaac | 120 |
| ttaatgttac ttgctttta cgaaaactca agtgtcaatt tgttctctca tttacacttt | 180 |
| ctatgcttat gacaccaaat tgaactctaa ttctactaaa acatgtttcc cttctctcgt | 240 | acaaatacta ataatcacac aaaaggaaag aaacaaatgg acaacaaagt tcgacc      296

<210> SEQ ID NO 9
<211> LENGTH: 543
<212> TYPE: DNA
<213> ORGANISM: Glycine max

<400> SEQUENCE: 9
gcatgaaaga aaaggatgac ttgtggactt ttgagagttt ttagatttgt gtttggtgaa      60
gtatatgtta ttgcaatgta cttcagataa tgtgaattat cttgtgtatc cgaatccaac     120
ttaatgttac ttgctttta cgaaaactca agtgtcaatt tgttctctca ttttacactt      180
ctatgcttat gacaccaaat tgaactctaa ttctactaaa acatgtttcc cttctctcgt     240
acaaatacta ataatcacac aaaaggaaag aaacaaatgg acaacaaagt tcgaccatta     300
taatcagtgt catagcattt caatttcttc tcctcactaa agcaggtaca aatatgtaat     360
tgtaatttca acatcgtaac atgttcttaa tggagtctga attctgaagt ttgatgctca     420
ctcaggttaa aagcaggtta taaaattaga ctaaatttta caaccagaaa tagaatctaa     480
gatacatgaa agcactttgg gttctcccat cttccttcaa tacaatggaa gccagaattg     540
tcc                                                                  543

<210> SEQ ID NO 10
<211> LENGTH: 933
<212> TYPE: DNA
<213> ORGANISM: Glycine max

<400> SEQUENCE: 10 aggggtaca ctttacataa ttgtatttca aaagtatttc ttcaagagta aacaaaagct      60
agcacagatg aaaaaacatt ttaaaaaaat tatttgacct tcatgtacga gtgctttcta    120
aattaaataa ttgactgtat agaggtgcct tctaaattct cctatattat ttcagcttgc    180
tttctttctt attttcccca gtcgctcacg aaaatctcct attctaatat cttgtgcagt    240
tttggcaatc aacatgtatt agtgagggtg tgactgtgat tactttgatt tttgaaacta    300
aaacaatacc aaacaaaaac cctctggtaa cgtgaagtaa tagtttttt ggtactgaaa     360
gaaaaagat agccatgtat ttatttagtt tattacaact aactatattt caatttgatg     420
taagtgcccc ctcattaaaa tggacctgtg taaccatcaa cctctagttc gctcttttca    480
ccatttgtct ctctgtctct gacttggcaa tatttgaaat tttgtggttc tcatttccct    540
tagtacaaca ccagatgtgg acccaaaaat atctcgagca ttgaaactaa ggatagccac    600
ataattcaag ccattttcca cgtcacctcc tcaatggaat agcataagaa ataagttaa     660
caaacatatc tactggaatc ccatagtcct acgtggaaga cccacattgg tcagaaaagc    720
agagaaagaa tctaacccat ttagtggatt atagggggtgc caagtgtacc aaacaaaatc    780
tgaaagcccc aatgagatag tagcaataga taggccaaga taagaacccc aaccacttga    840
agcccatata aataaaccccc cacacaactt cactgaatca ctcacaactc cataacacaa    900
ggcagaaagc aagctcatcc tagagttta aaa                                  933

<210> SEQ ID NO 11
<211> LENGTH: 2003
<212> TYPE: DNA
<213> ORGANISM: Artificial Sequence
<220> FEATURE:
<223> OTHER INFORMATION: Synthesized DNA fragment

<400> SEQUENCE: 11

```
ggtccggcaa ataatgattt tattttgact gatagtgacc tgttcgttgc aacaaattga    60
taagcaatgc ttttttataa tgccaacttt gtacaaaaaa gcaggcttct agacctaggt   120
ggagtcatca cgcagactat ctcagcatgt gcgtagcacg cggccgcctt catataaatg   180
tatttcaaaa gtatttcttc tagaataaac taaagctatt acagatgaaa aattcttaaa   240
aaattatttg accttcatat atgggtcctt ttctaattaa taattaacta tataggtgca   300
ttctaaatgc tcctatatta tctgctttct cctcttcttt cctttttcc tagtcgctca    360 cgaaaatctc ctataatcct ctgcagtttt cgaaatcaat aaccgactcc tagaacctgt   420
ccatgtctaa cttaataaat cgtgagggtg tgattgtgat tactttgaat ctttaatttt   480
tgacattaaa acaagaccaa acaaaaacct tcaggttacg tgagactcca acctacccaa   540
gttatgtatt agttttttcct ggtccagaag aaaagagcca tgcattagtt tattacaact   600
aactatattt caatttcatg taagtgtgcc ccctcattaa aatcgacctg tgtaaccatc   660
aacctgtagt tcgctctttt caccatttgt ctctctgtct ttatcttccc tcccccattg   720
ccaatatttg ttgcaataca acatctctcc gttgcaatca ctcatttcaa attttgtggt   780
tctcatttgc cctagtacaa cattagatgt ggacccaaaa atatctcaca ttgaaagcat   840
atcagtcaca caattcaatc aatttttttcc acatcacctc ctaaattgaa taacatgaga   900
aaaaaatagc taagtgcaca tacatatcta ctggaatccc atagtcctac gtggaagacc   960
cacattggcc acaaaaccat acgaagaatc taacccattt agtggattat gggggtgcca  1020
agtgtaccaa acaaaatctc aaaccccccaa tgagattgta gcaatagata gcccaagata  1080
agaacccaac cacttcaacc ccatataaat aaacccggac acaacttcac caagtcactc  1140
accacttcaa aacactcata acacaaagca caaagcaaag ctcatccttg agttaaaaaa  1200
ggatccaaac accatggtga cttaaggtag ttagcttaat cacctagagc tcggttaccc  1260
aacttcgtcc ccggaaagtg agcgtcaaag aacgaaatga cttttgagag ttttttagatt  1320 tgtgtttggt gaagtacttc agataatgtg aattatcttg tgtatccgaa tccaacttaa  1380
tgttacttgc ttttttacaaa actcaagtgt caatttgttc tctcattttta tacttctaag  1440 cttttgacgc cacattgaat ttgaactcta attgaactaa aaaatgtttc ccttctctca  1500
tactaatact aatactaagc agggccacta ataatcacac aaaaggaaag aaacaatatg  1560
acaacaaaat tcgaccatta ttatcactgt catcgaattc caatttcttc tcctcactaa  1620 acaggtatg tatatgtaat tgtaatttca acatcgtcac atgttcttaa tggagtctga  1680
attttgaagt ttgatgcttg ctcctgttaa aaggatgtta aaattagacc aaactttatt  1740
accagcaata gaatctcata tacgagaaag tactttgggt tctcccatct tccttcactc  1800
cagtggtagc cagaagcggc cgcttaatta actactgtca ctgaggccgt agacgagtac  1860
ggactgatct aactagtgct agcctcgagg tcgacaccca gctttcttgt acaaagttgg  1920
cattataaga aagcattgct tatcaatttg ttgcaacgaa caggtcacta tcagtcaaaa  1980
taaaatcatt atttgggcgc gcc                                          2003
```

<210> SEQ ID NO 12
<211> LENGTH: 1686
<212> TYPE: DNA
<213> ORGANISM: Artificial Sequence
<220> FEATURE:
<223> OTHER INFORMATION: fusion reporter gene

<400> SEQUENCE: 12

```
tcaaaccaag gcagcaccct cagtttctgg gcgtccagcg agtctggagt gccacatcac    60
acgtggcaac ttgaaatccc agggctcagc acggtggagc aaacagcggt tgtcccacac   120
aaccacatct ccagcagccc attggtgagc atggactctg ggagcctggc aggcccagtc   180
aacaagtcct tcaaggaagc gctctgattc agctgcatcc atgccaggga tggcatgggc   240
atggcggccg atcaagaggc tgggccttcc agtctcagga tgcaccttga ccaatggtct   300
gagaggagtt gcagtggtgt ccatgccata acctatgtag gctgacccgg cctgttggac   360
atgtcccaac ttgctctgag aatacacaag ggagtgacga gcagaccttt ggtgaacaag   420
agcacgggtt gcctcatcaa gggcatcgta ggctgccctc atgtcagcaa agcaggttct   480
gcccccaact gctgggacaa cttctgcgct gaacacagct ccttgagcca tgactggcat   540
gtaggttgag tcggcgtgcc aggccatgtt gcccacaatg accttcatca tgtcatccca   600
ctcagcagga gagtgctggc gcactgtgcc atctgccttg acattggata tggcaacaat   660
gtcacctccg ccaatcctct caattgctcc aaagcgttta gcaaaggtaa tctgttggtc   720
attgctgagg tgttgcccag ggaagatcaa gagtgcatgt tgaagccagg ctgcatggag   780
ggcagcgaaa ccagcatcgt caagtgtggc aaggtgaaca ccagtgactg tggcacccaa   840
ggtggcacca gtgggtgtga tttggagagt ggtctgagcc atggcagctg ccttagctgc   900
ggcttctttt gcggcagcct cctttgcagc ggcttccttg gctgcagcct ctttagcggc   960
tgcttcctcg gcgagattca acttgtgtcc gagcttgctg gaaggtcac agtaacgagc   1020 aacagccacc tcatgctgtt cgacataggt ttccttgtct gcctccttga tcctttccaa  1080
gcgatgatcc acatagtaga cgccaggcat cttgagattc ttagcaggtt tctttgagcg  1140
gtatgtggtc ttgaagttgc aaatcaaatg ccacctcca accaacttga gtgccatatc  1200
agacctcccc tcaagcccac catcggctgg gtaaagcatc tcggtgtttg cttcccatcc  1260
aagggttttc ttctgcataa ctggtccatt tgatggaaag ttcacacctc taatcttgac  1320
attgtagatg agacacccat cttgcaaaga agtgtcttga gtagcggtca acacgccacc  1380
atcttcgtaa gttgtaacac gctcccatgt gaaaccctca ggaaaagact gcttaaagaa  1440
gtcgggaatc ccttgtgtgt gattgatgaa agttctggag ccatacatga agctagtggc  1500
aagtatgtcg aaggcaaatg ggagtggtcc accctcaacc actttgatcc tcatggtctg  1560
ggttccctca taaggcttgc cttctcccctc ggatgtgcat ttgaagtgat gattgttgac  1620
agtgccctcc atgtagagct tcatgtgcat gttctctttg ataagttcct cgcctttgct  1680
caccat                                                              1686
```

<210> SEQ ID NO 13
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 13
acaagagtgg attgatgatc tagaga                                         26

<210> SEQ ID NO 14
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 14
ctttgatgcc tatgtgacac gtaaac                                          26

<210> SEQ ID NO 15
<211> LENGTH: 29
<212> TYPE: DNA
<213> ORGANISM: Artificial Sequence
<220> FEATURE:
<223> OTHER INFORMATION: synthesized probe oligonucleotide

<400> SEQUENCE: 15
ccagcgtaag caataccagc cacaacacc                                       29

<210> SEQ ID NO 16
<211> LENGTH: 21
<212> TYPE: DNA
<213> ORGANISM: Artificial Sequence
<220> FEATURE:
<223> OTHER INFORMATION: synthesized primer oligonucleotide

<400> SEQUENCE: 16
cgccgaagta tcgactcaac t                                               21

<210> SEQ ID NO 17
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 17
gcaacgtcgg ttcgagatg                                                  19

<210> SEQ ID NO 18
<211> LENGTH: 24
<212> TYPE: DNA
<213> ORGANISM: Artificial Sequence
<220> FEATURE:
<223> OTHER INFORMATION: synthesized probe oligonucleotide

<400> SEQUENCE: 18
tcagaggtag ttggcgtcat cgag                                            24

<210> SEQ ID NO 19
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 19
gaggattagg gtttcaacgg ag                                              22

<210> SEQ ID NO 20
<211> LENGTH: 21
<212> TYPE: DNA
<213> ORGANISM: Artificial Sequence
<220> FEATURE:
<223> OTHER INFORMATION: synthesized primer oligonucleotide

<400> SEQUENCE: 20
gagaattgag ctgagacgag g                                               21

<210> SEQ ID NO 21
<211> LENGTH: 25
<212> TYPE: DNA

```
<213> ORGANISM: Artificial Sequence
<220> FEATURE:
<223> OTHER INFORMATION: synthesized probe oligonucleotide

<400> SEQUENCE: 21
agagaagttt cgacggattt cgggc                                      25

<210> SEQ ID NO 22
<211> LENGTH: 29
<212> TYPE: DNA
<213> ORGANISM: Artificial Sequence
<220> FEATURE:
<223> OTHER INFORMATION: synthesized primer oligonucleotide

<400> SEQUENCE: 22
acaagagtgg attgatgatc tagagaggt                                  29

<210> SEQ ID NO 23
<211> LENGTH: 29
<212> TYPE: DNA
<213> ORGANISM: Artificial Sequence
<220> FEATURE:
<223> OTHER INFORMATION: synthesized primer oligonucleotide

<400> SEQUENCE: 23
ctttgatgcc tatgtgacac gtaaacagt                                  29

<210> SEQ ID NO 24
<211> LENGTH: 29
<212> TYPE: DNA
<213> ORGANISM: Artificial Sequence
<220> FEATURE:
<223> OTHER INFORMATION: synthesized probe oligonucleotide

<400> SEQUENCE: 24
agggtgttgt ggctggtatt gcttacgct                                  29

<210> SEQ ID NO 25
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 25
cagagtccat gctcaccaat                                            20

<210> SEQ ID NO 26
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 26
acgtggcaac ttgaaatcc                                             19

<210> SEQ ID NO 27
<211> LENGTH: 24
<212> TYPE: DNA
<213> ORGANISM: Artificial Sequence
<220> FEATURE:
<223> OTHER INFORMATION: synthesized probe oligonucleotide

<400> SEQUENCE: 27
tggagatgtg gttgtgtggg acaa                                       24
```

```
<210> SEQ ID NO 28
<211> LENGTH: 31
<212> TYPE: PRT
<213> ORGANISM: Artificial Sequence
<220> FEATURE:
<223> OTHER INFORMATION: synthesized helical peptide linker

<400> SEQUENCE: 28

Leu Ala Glu Glu Ala Ala Ala Lys Glu Ala Ala Ala Lys Glu Ala Ala
1               5                   10                  15

Ala Lys Glu Ala Ala Ala Lys Glu Ala Ala Ala Lys Ala Ala Ala
            20                  25                  30
```

COMPOSITIONS AND METHODS FOR EXPRESSING TRANSGENES USING REGULATORY ELEMENTS FROM CHLOROPHYLL BINDING AB GENES

CROSS REFERENCE TO RELATED APPLICATION

The present application claims priority to the benefit of U.S. Provisional Patent Application Ser. No. 62/552,692 filed Aug. 31, 2017 the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 18 KB ASCII (Text) file named "77714-US-PCT-20200806-Sequence-Listing-ST25.txt" created on Aug. 6, 2020.

BACKGROUND

Many plant species are capable of being transformed with transgenes to introduce agronomically desirable traits or characteristics. Improved varieties of many plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of the transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species expressing multiple transgenes engineered as a trait stack are desirable.

Regulatory elements that support a wide range of expression levels for ubiquitous, organ/tissue specific, and/or developmentally regulated expression patterns present valuable tools in plant biotechnology. Some examples of broad regulatory patterns are ubiquitous expression in most of the tissues/organs, preferential expression in the above ground green tissues, preferential expression in below ground root tissues, expression in developing seeds, etc.

In addition to the need for diverse regulatory expression patterns and levels of expression, the optimal transgene expression may require minimizing or avoiding the repeated use of the same promoter in the multi-transgene stacks. While, expression of multiple transgenes of interest may be controlled by repeatedly using the same promoter, the repeated use of promoters comprising sequences that share a high level of sequence identity may lead to homology-based gene silencing (HBGS). HBGS is most likely to arise when multiple transgenes, regulated by promoters with high levels of sequence identity, are introduced into a genome. HBGS has been observed to occur extensively in transgenic plants (Peremarti et al, (2010), Plant Molecular Biology, 73, 363-378).

To diversify the use of upstream (promoters and 5' UTRs) and downstream (3' UTRs that are embedded in a larger terminator fragment) regulatory elements, we identified and characterized the described regulatory elements from the *Glycine max* chlorophyll binding Ab genes. Further described are constructs and methods utilizing chlorophyll binding Ab regulatory elements.

SUMMARY

Disclosed herein are regulatory elements, constructs and methods for expressing a transgene in plant cells and/or plant tissues. In one embodiment regulatory elements of a chlorophyll binding Ab gene are purified from a *Glycine max* chlorophyll binding Ab gene DNA and recombined with sequences not natively linked to said regulatory elements to create an expression cassette for expressing transgenes in plant cells non-native to the chlorophyll binding Ab regulatory sequences. In one embodiment an expression vector is provided wherein the regulatory elements of a chlorophyll binding Ab gene are operably linked to a polylinker sequence. Such an expression vector facilitates the insertion of a gene or gene cassette into the vector in an operably linked state with the chlorophyll binding Ab gene regulatory sequences.

In an embodiment, an expression cassette is provided comprising a *Glycine max* chlorophyll binding Ab promoter, 5' UTR and a transcription termination fragment (terminator) containing a 3' UTR and polyadenylation signals. In an embodiment, a gene expression cassette is provided comprising a *Glycine max* chlorophyll binding Ab promoter and 5' UTR operably linked to a transgene. In an embodiment, a gene expression cassette includes a *Glycine max* chlorophyll binding Ab 5' UTR operably linked to a promoter. In an embodiment, a construct includes a gene expression cassette comprising *Glycine max* chlorophyll binding Ab terminator. In an embodiment, a gene expression cassette includes *Glycine max* chlorophyll binding Ab terminator operably linked to a transgene. In an embodiment, a gene expression cassette includes at least one, two, three, four, five, six, seven, eight, nine, ten, or more transgenes.

In an embodiment, a gene expression cassette includes independently a) a *Glycine max* chlorophyll binding Ab promoter, b) a *Glycine max* chlorophyll binding Ab 5' UTR, and c) a *Glycine max* chlorophyll binding Ab terminator.

Methods of expressing a transgene in a plant comprising transforming the plant with the *Glycine max* promoters, 5' UTRs, and/or terminator operably linked to the transgene are disclosed herein. Methods of expressing a transgene by growing plants comprising the *Glycine max* promoters, 5' UTRs, terminator, and combinations thereof are disclosed herein. Methods of culturing plant tissues and cells expressing a transgene using the *Glycine max* promoter, 5' UTRs, and terminator are also disclosed herein.

In accordance with one embodiment a bacterial cell, plant cell, plant, or plant tissue is provided comprising a promoter operably linked to a non-chlorophyll binding Ab transgene, wherein the promoter comprises SEQ ID NOs:1, 5, 6, or 10-11, or a sequence that has 95% sequence identity with SEQ ID NOs:1, 5, 6, or 10-11. In accordance with one embodiment a plant, plant part or plant cell is provided comprising SEQ ID NOs:1, 5, 6, or 10-11, or a sequence that has 95% sequence identity with SEQ ID NOs:1, 5, 6, or 10-11, operably linked to a transgene. In one embodiment the plant is a soybean variety.

In one embodiment a plant, plant tissue, or plant cell is provided comprising a promoter operably linked to a non-chlorophyll binding Ab transgene, wherein the promoter consists of SEQ ID NOs:1, 5, 6, or 10-11. In one embodiment the promoter is operably linked to a first end of a transgene, wherein the second end of the transgene is operably linked to a 3' untranslated region or terminator comprising SEQ ID NOs:3, 4, 8, or 9.

BRIEF DESCRIPTION OF THE FIGURES

FIG. 2 is an alignment of upstream DNA sequence for SEQ ID NO:5 (candidate promoter and 5'UTR from Glyma08g08770) and SEQ ID NO:10 (candidate promoter and 5'UTR from Glyma05g25810). The figure shows the alignment of upstream regulatory sequences (promoters and 5' UTRs) identified herein. The *Glycine max* chlorophyll binding Ab promoter sequences are disclosed herein as SEQ ID NO:1 (candidate promoter from Glyma08g08770, GmCAB) and SEQ ID NO:6 (candidate promoter from Glyma05g25810).

DETAILED DESCRIPTION

Definitions

Figure 1:
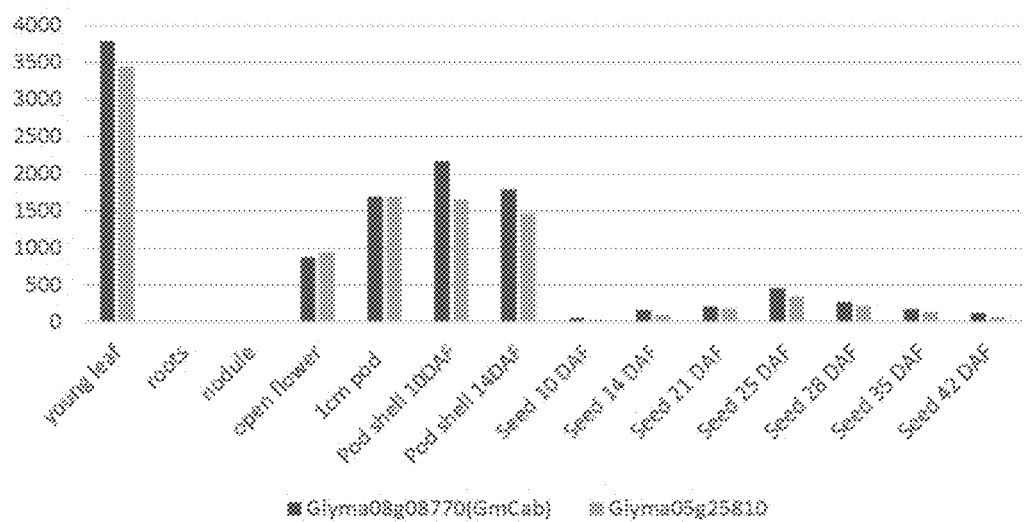
FIG. 1 is a graph illustrating the expression pattern of two *Glycine max* endogenous chlorophyll binding Ab genes. Expression for soybean genes was obtained from soybean RNA-Seq expression atlas that mapped to *Glycine max* genome assembly Glyma1.01 produced by Severin et al, (2010), BMC Plant Biol, 10, 160. DAF stands for days after pollination. Y-axis indicates reads/Kb/Million (RPKM).
Figure 1:
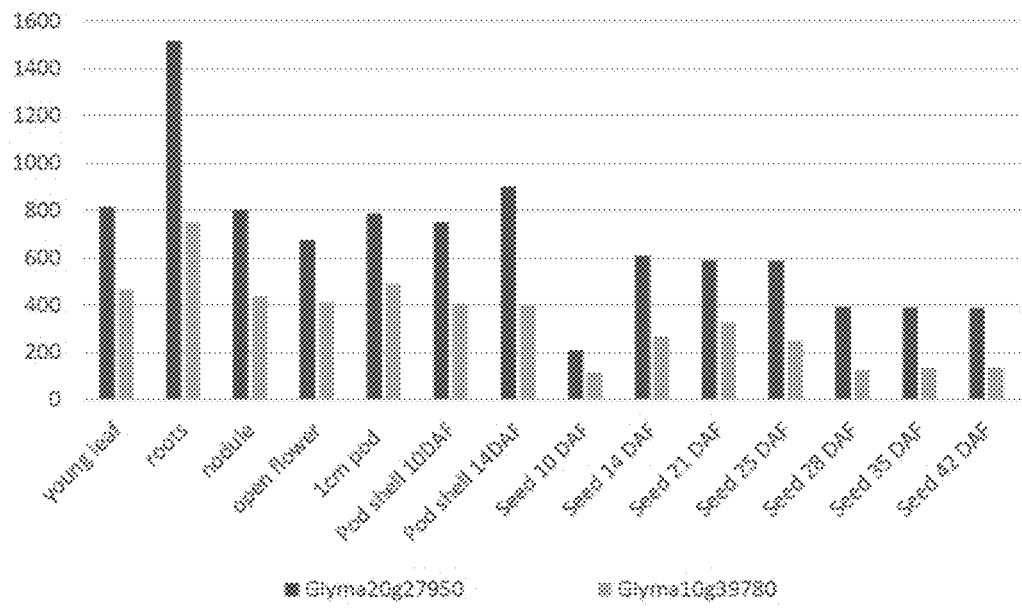

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

A "promoter" is a DNA regulatory element capable of binding RNA polymerase in a cell and initiating transcription of a downstream (3' direction) coding sequence. A promoter may contain specific sequences that are recognized by transcription factors. These factors may bind to a promoter DNA sequence, which results in the recruitment of RNA polymerase. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (defined for example, by mapping with nuclease S1), as well as protein binding domains (consensus sequences) responsible for the binding of RNA polymerase. The promoter may be operatively associated with other expression control sequences, including enhancer and repressor sequences.

For the purposes of the present disclosure, a "gene," includes a DNA region encoding a gene product (see infra), as well as all DNA regions that regulate the production of the gene product (excluding promoters), whether or not such regulatory sequences are adjacent to coding and/or transcribed sequences. Accordingly, a gene includes, but is not necessarily limited to, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-tolerance gene). In yet another example, a transgene is an interfering RNA (iRNA) molecule (e.g., antisense RNA, double-stranded RNA (dsRNA), short-interfering RNA (siRNA), short hairpin RNA (shRNA), micro RNA (miRNA), and hairpin RNA (hpRNA)) nucleic acid sequence, wherein expression of the iRNA nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-chlorophyll binding Ab transgene" is any transgene that is not naturally expressed by *Glycine max* regulatory elements of the present invention, does not encode a chlorophyll binding Ab protein, and/or has less than 80% sequence identity with the *Glycine max* chlorophyll binding Ab coding sequence.

"Gene expression" as defined herein is the conversion of the information, contained in a gene, into a gene product.

A "gene product" as defined herein is any product produced by the gene. For example the gene product can be the direct transcriptional product of a gene (e.g., mRNA, tRNA, rRNA, iRNA, ribozyme, structural RNA or any other type of RNA) or a protein produced by translation of an mRNA. Gene products also include RNAs that are modified, by processes such as capping, polyadenylation, methylation, and editing, and proteins modified by, for example, methylation, acetylation, phosphorylation, rubisco activation, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "intron" is defined as any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "5' untranslated region" or "5' UTR" is defined as a regulatory element comprising the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3' untranslated region" or "3' UTR" is defined as a regulatory element comprising the untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "terminator" is defined as a regulatory element comprising the untranslated segment in a 3' terminus of the pre-mRNAs or mature mRNAs containing 3' UTRs that may arise from transcription termination and polyadenylation at multiple positions with the transcription terminator fragment.

As used herein, the term "polyadenylation signal" designates a regulatory element comprising a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3): 1457-1468.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified," as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to other polynucleotides, polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

As used herein, the terms "homology-based gene silencing" or "HBGS" are generic terms that include both transcriptional gene silencing and posttranscriptional gene silencing. Silencing of a target locus by an unlinked silencing locus can result from transcription inhibition (transcriptional gene silencing; TGS) or mRNA degradation (post-transcriptional gene silencing; PTGS), owing to the production of iRNA corresponding to promoter or transcribed sequences, respectively. Involvement of distinct cellular components in each process suggests that iRNA-induced TGS and PTGS likely result from the diversification of an ancient common mechanism. A single transgene locus can be described to trigger both TGS and PTGS, owing to the production of iRNA corresponding to promoter and transcribed sequences of different target genes.

As used herein, the terms "nucleic acid molecule", "nucleic acid", or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position," refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between an oligonucleotide and the DNA or RNA target. Oligonucleotides need not be 100% complementary to its target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize. In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, an oligonucleotide is typically referred to as a "primer," which allows a DNA polymerase to extend the oligonucleotide and replicate the complementary strand.

As used herein, the terms "Polymerase chain reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (TexasRed®, Fluorescein isothiocyanate, etc.). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "sequence identity" or "identity" can be used interchangeably and refer to nucleic acid residues in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (which does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to two components that have been placed into a functional relationship with one another. The term, "operably linked," when used in reference to a regulatory sequence and a coding sequence, means that the regulatory sequence affects the expression of the linked coding sequence. "Regulatory sequences," "regulatory elements", or "control elements," are used interchangeably and refer to nucleic acid sequences that influence the timing and level/amount of transcription, RNA processing or stability, or translation of the associated coding sequence. Regulatory sequences may include promoters; translation leader sequences; 5' and 3' untranslated regions, introns; enhancers; stem-loop structures; repressor binding sequences; termination sequences; polyadenylation recognition sequences; etc. Particular regulatory sequences may be located within, upstream and/or downstream of a coding sequence operably linked thereto. Also, particular regulatory sequences operably linked to a coding sequence may be located on the associated complementary strand of a double-stranded nucleic acid molecule. Linking can be accomplished by ligation at convenient restriction sites. If such sites do not exist, synthetic oligonucleotide adaptors or linkers are used in accordance with conventional practice. However, elements need not be contiguous to be operably linked.

As used herein, the term "transformation" encompasses all techniques by which a nucleic acid molecule can be introduced into such a cell. Examples include, but are not limited to: transfection with viral vectors; transformation with plasmid vectors; electroporation; lipofection; microinjection; *Agrobacterium*-mediated transfer; direct DNA uptake; whiskers-mediated transformation; and microprojectile bombardment.

The terms "polylinker" or "multiple cloning site" as used herein defines a cluster of three or more Type-2 restriction enzyme sites located within 10 nucleotides of one another on a nucleic acid sequence. Constructs comprising a polylinker are utilized for the insertion and/or excision of nucleic acid sequences such as the coding region of a gene.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI The term "vector" is used interchangeably with the terms "construct", "cloning vector", "nucleic acid vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, iRNA molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

The term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide tolerance including bar or pat (tolerance against glufosinate ammonium or phosphinothricin), acetolactate synthase (ALS, tolerance against inhibitors such as sulfonylureas (SUs), imidazolinones (IMIs), triazolopyrimidines (TPs), pyrimidinyl oxybenzoates (POBs), and sulfonyl amino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, red fluorescent protein (RFP), β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

As used herein, the terms "cassette", "expression cassette" and "gene expression cassette" refer to a segment of DNA that can be inserted into a nucleic acid or polynucleotide randomly or at specific restriction sites or by homologous recombination (e.g., within a vector or within a genome). As used herein the segment of DNA can comprise a polynucleotide that encodes a gene product (e.g., a polypeptide or an iRNA) of interest, and the cassette can include restriction sites or homology sequences designed to ensure insertion of the cassette in the proper reading frame for transcription and translation. In an embodiment, an expression cassette can include a polynucleotide that encodes a gene product of interest and having elements in addition to the polynucleotide that facilitate transformation of a particular host cell. In an embodiment, a gene expression cassette may also include elements that allow for enhanced expression of a polynucleotide encoding a gene product of interest in a host cell. These elements may include, but are not limited to: a promoter, a minimal promoter, an enhancer, a response element, a terminator sequence, a polyadenylation sequence, a 5' UTR, a 3' UTR, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant (and any descendant), cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast," as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls, which has the potency for regeneration into cell culture or a whole plant.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

EMBODIMENTS

As disclosed herein novel recombinant expression cassettes are provided for expressing a non-chlorophyll binding Ab transgene using the regulatory sequences of a chlorophyll binding Ab gene from *Glycine max*. These cassettes can be used to produce vectors and to transform cells, including plant cells, to produce complete organisms that express the transgene gene product in their cells.

Regulatory Elements

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in transgenic crops to drive the expression of multiple genes.

Development of transgenic products is becoming increasingly complex, which requires stacking multiple transgenes into a single locus. Traditionally, each transgene usually requires a promoter for expression wherein multiple promoters are required to express different transgenes within one gene stack. With an increasing size of gene stacks, this frequently leads to repeated use of the same promoter to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

It is desirable to use diversified promoters for the expression of different transgenes in a gene stack. In an embodiment, chlorophyll binding Ab (GmCAB) regulatory sequences (e.g., promoter, 5' UTR, 3' UTR and transcription termination sequence (terminator)) obtained from soybean can drive transcription of a transcription unit or multiple transcription units, including protein coding sequence, and iRNA sequences.

Provided are methods and expression cassettes and constructs using a chlorophyll binding Ab (GmCAB) promoter, 5' UTR, 3' UTR, and terminator to express non-chlorophyll binding Ab transgenes in a plant or plant part. In an embodiment, a promoter can be the *Glycine max* chlorophyll binding Ab (GmCAB; SEQ ID NO:1) promoter and 5' UTR (SEQ ID NO:2).

```
CTTCATATAAATGTATTTCAAAAGTATTTCTTCTAGAATAAACTAAAGC

TATTACAGATGAAAAATTCTTAAAAAATTATTTGACCTTCATATATGGG

TCCTTTTCTAATTAATAATTAACTATATAGGTGCATTCTAAATGCTCCT

ATATTATCTGCTTTCTCCTCTTCTTTCCTTTTTTCCTAGTCGCTCACGA

AAATCTCCTATAATCCTCTGCAGTTTTCGAAATCAATAACCGACTCCTA

GAACCTGTCCATGTCTAACTTAATAAATCGTGAGGGTGTGATTGTGATT

ACTTTGAATCTTTAATTTTTGACATTAAAACAAGACCAAACAAAAACCT

TCAGGTTACGTGAGACTCCAACCTACCCAAGTTATGTATTAGTTTTTCC

TGGTCCAGAAGAAAAGAGCCATGCATTAGTTTATTACAACTAACTATAT

TTCAATTTCATGTAAGTGTGCCCCCTCATTAAAATCGACCTGTGTAACC

ATCAACCTGTAGTTCGCTCTTTTCACCATTTGTCTCTCTGTCTTTATCT

TCCCTCCCCCATTGCCAATATTTGTTGCAATACAACATCTCTCCGTTGC

AATCACTCATTTCAAATTTTGTGGTTCTCATTTGCCCTAGTACAACATT

AGATGTGGACCCAAAAATATCTCACATTGAAAGCATATCAGTCACACAA

TTCAATCAATTTTTTCCACATCACCTCCTAAATTGAATAACATGAGAAA

AAAATAGCTAAGTGCACATACATATCTACTGGAATCCCATAGTCCTACG

TGGAAGACCCACATTGGCCACAAAACCATACGAAGAATCTAACCCATTT

AGTGGATTATGGGGGTGCCAAGTGTACCAAACAAAATCTCAAACCCCCA

ATGAGATTGTAGCAATAGATAGCCCAAGATAAGAACCCAACCACTTCAA

CCCCATATAAATAAACCCGGACACAACTTCACCAAGTCACTCACCACTT

CAAAACACTCATAACACAAAGCACAAAGCAAAGCTCATCCTTGAGTTAA

AAAA (SEQ ID NO: 5, which is GmCAB promoter together with the 5' UTR. The 5'UTR sequence is bolded).
```

In an embodiment, a nucleic acid construct is provided comprising a chlorophyll binding Ab promoter and 5' UTR.

In an embodiment, the chlorophyll binding Ab promoter and 5' UTR is a *Glycine max* chlorophyll binding Ab promoter and 5' UTR. In an embodiment, a nucleic acid construct is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1, 5, or 6. In an embodiment, a nucleic acid construct is provided comprising a chlorophyll binding Ab and 5' UTR promoter that is operably linked to a polylinker. In an embodiment, a gene expression cassette is provided comprising a chlorophyll binding Ab promoter and 5' UTR that is operably linked to a non-chlorophyll binding Ab transgene. In one embodiment the promoter consists of SEQ ID NOs:1, 5, 6, or 10-11. In an illustrative embodiment, a gene expression cassette comprises a chlorophyll binding Ab promoter and 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an iRNA, or combinations thereof.

Transgene expression may also be regulated by the 3'-untranslated gene region (i.e., 3' UTR) located downstream of the gene's coding sequence. Both a promoter and a 3' UTR can regulate transgene expression. While a promoter is necessary to drive transcription, a transcription terminator fragment containing 3' UTR gene region contained within a terminator fragment can terminate transcription and initiate polyadenylation of a resulting mRNA transcript for translation and protein synthesis. A transcription terminator fragment containing 3' UTR gene region aids stable expression of a transgene.

In an embodiment, a nucleic acid construct is provided comprising a chlorophyll binding Ab promoter and 5' UTR as described herein and a terminator fragment containing a 3' UTR. In an embodiment, the nucleic acid construct comprises a chlorophyll binding Ab terminator fragment containing a 3' UTR. In an embodiment, the chlorophyll binding Ab terminator fragment containing transcription terminator fragment containing a 3' UTR is a *Glycine max* chlorophyll binding Ab 3' UTR. In an embodiment, a terminator fragment containing transcription terminator fragment containing a 3' UTR can be the *Glycine max* chlorophyll binding Ab (GmCAB) terminator fragment containing a 3' UTR.

(SEQ ID NO: 4)
CAACTTCGTCCCCGGAAAGTGAGCGTCAAAGAACGAAATGACTTTTGAGA

GTTTTTAGATTTGTGTTTGGTGAAGTACTTCAGATAATGTGAATTATCTT

GTGTATCCGAATCCAACTTAATGTTACTTGCTTTTTACAAAACTCAAGTG

TCAATTTGTTCTCTCATTTTATACTTCTAAGCTTTTGACGCCACATTGAA

TTTGAACTCTAATTGAACTAAAAAATGTTTCCCTTCTCTCATACTAATAC

TAATACTAAGCAGGGCCACTAATAATCACACAAAAGGAAAGAAACAATAT

GACAACAAAATTCGACCATTATTATCACTGTCATCGAATTCCAATTTCTT

CTCCTCACTAAAACAGGTATGTATATGTAATTGTAATTTCAACATCGTCA

CATGTTCTTAATGGAGTCTGAATTTTGAAGTTTGATGCTTGCTCCTGTTA

AAAGGATGTTAAAATTAGACCAAACTTTATTACCAGCAATAGAATCTCAT

ATACGAGAAAGTACTTTGGGTTCTCCCATCTTCCTTCACTCCAGTGGTAG

CCAGAA GmCAB terminator sequence: 3' UTR is bolded.

In an embodiment, a nucleic acid construct is provided comprising a chlorophyll binding Ab promoter and 5' UTR as described herein and a transcription terminator fragment containing a 3' UTR, wherein the transcription terminator fragment containing the 3' UTR is at least 80%, 85%, 90%, 91%, 92%, 93%, 94%, 95%, 96%, 97%, 98%, 99%, 99.5%, 99.8%, or 100% identical to SEQ ID NOs:3, 4, 8, or 9. In an embodiment, a nucleic acid construct is provided comprising a chlorophyll binding Ab promoter and 5' UTR as described herein and the transcription terminator fragment containing the 3' UTR wherein the chlorophyll binding Ab promoter, 5' UTR and 3' UTR are both operably linked to opposite ends of a polylinker. In an embodiment, a gene expression cassette is provided comprising a chlorophyll binding Ab promoter and 5' UTR as described herein and a 3' UTR, wherein the chlorophyll binding Ab promoter, 5' UTR and 3' UTR are operably linked to opposite ends of a non-chlorophyll binding Ab transgene. In one embodiment the 3' UTR, consists of SEQ ID NO:3. In another embodiment, a gene expression cassette is provided comprising a chlorophyll binding Ab promoter and 5' UTR as described herein and a 3' UTR, wherein the chlorophyll binding Ab promoter and 5' UTR comprises SEQ ID NO:5 and the 3' UTR comprises SEQ ID NO:3 wherein the promoter and 3' UTR are operably linked to opposite ends of a non-chlorophyll binding Ab transgene. In one embodiment the 3' UTR, consists of SEQ ID NO:3. In yet another embodiment the promoter consists of SEQ ID NO:1 and the 3' UTR, consists of SEQ ID NO:3. In an illustrative embodiment, a gene expression cassette comprises a chlorophyll binding Ab transcription terminator fragment containing a 3' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an iRNA, or combinations thereof. In a further embodiment the transgene is operably linked to a chlorophyll binding Ab promoter and 5' UTR and a transcription terminator fragment containing a 3' UTR from the same chlorophyll binding Ab gene isolated from *Glycine max*.

In an embodiment, a nucleic acid construct is provided comprising a *Glycine max* chlorophyll binding Ab promoter (e.g., SEQ ID NOs:1 or 6) operably linked to 5' UTRs from *Glycine max* chlorophyll binding Ab gene, wherein the 5' UTR is at least 80%, 85%, 90%, 91%, 92%, 93%, 94%, 95%, 96%, 97%, 98%, 99%, 99.5%, 99.8%, or 100% identical to SEQ ID NOs:2 or 7. In an embodiment, a nucleic acid construct is provided comprising a chlorophyll binding Ab promoter as described herein and fragment containing a 5' UTR wherein the 5' UTR is a chlorophyll binding Ab 5' UTR. In an embodiment, a gene expression cassette is provided comprising a chlorophyll binding Ab promoter as described herein and a 5' UTR, wherein the chlorophyll binding Ab promoter and 5' UTR are both operably linked to the downstream reporter gene that is a non-chlorophyll binding Ab transgene. In one embodiment *Glycine max* chlorophyll binding Ab promoter comprises SEQ ID NOs:1 or 6. In one embodiment, a gene expression cassette is provided comprising a chlorophyll binding Ab promoter as described herein and a 5' UTR, wherein the chlorophyll binding Ab promoter comprises SEQ ID NOs:1 or 6 and the 5' UTR comprises SEQ ID NOs:2 or 7 wherein the promoter and 5' UTR are operably upstream of a non-chlorophyll binding Ab transgene. In one embodiment *Glycine max* chlorophyll binding Ab promoter consists of SEQ ID NOs:1 or 6 and the 5' UTR, consists of SEQ ID NOs:2 or 7. In an illustrative embodiment, a gene expression cassette comprises a chlorophyll binding Ab promoter linked to *Glycine max* chlorophyll binding Ab 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an interfering RNA (e.g., an artificial micro RNA, a hairpin RNA, or an antisense RNA), or combinations thereof. In a further embodiment, the transgene is operably linked to a chlorophyll binding Ab 5' UTR and a transcription terminator fragment containing 3' UTR from the same chlorophyll binding Ab gene isolated from *Glycine max*.

Transgene expression may also be regulated by a 5' UTR region located downstream of the promoter sequence. Both a promoter and a 5' UTR can regulate transgene expression. While a promoter is necessary to drive transcription, the presence of a 5' UTR can increase expression levels resulting in mRNA transcript for translation and protein synthesis. A 5' UTR gene region aids stable expression of a transgene.

In an embodiment, a nucleic acid construct is provided comprising a *Glycine max* chlorophyll binding Ab promoter as described herein and a 5' UTR. In one embodiment the 5' UTR is operably linked to the 3' end of the promoter. In an embodiment, a nucleic acid construct is provided comprising a *Glycine max* chlorophyll binding Ab 5' UTR operably linked to the 3' end of a *Glycine max* chlorophyll binding Ab promoter isolated from *Glycine max* or a derivative of such promoter sequence, as described herein.

In an embodiment, a 5' UTR can be the *Glycine max* chlorophyll binding Ab (GmCAB) 5' UTR.

```
                                              (SEQ ID NO: 2)
ATAAGAACCCAACCACTTCAACCCCATATAAATAAACCCGGACACAACTT

CACCAAGTCACTCACCACTTCAAAACACTCATAACACAAAGCACAAAGCA

AAGCTCATCCTTGAGTTAAAAAA In an embodiment, a 5' UTR can be the Glycline max chlorophyll binding Ab (GmCAB) 5' UTR..
```

In an embodiment, a nucleic acid construct is provided comprising a chlorophyll binding Ab promoter as disclosed herein and a 5' UTR, wherein the 5' UTR is at least 80%, 85%, 90%, 91%, 92%, 93%, 94%, 95%, 96%, 97%, 98%, 99%, 99.5%, 99.8%, or 100% identical to SEQ ID NO:2 or 7. In an embodiment, a nucleic acid construct is provided comprising chlorophyll binding Ab promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6 and a 5' UTR operably linked to a polylinker. In an embodiment, a gene expression cassette is provided comprising a chlorophyll binding Ab promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6 and a 5' UTR sequence operably linked to a non-chlorophyll binding Ab transgene. In one embodiment the 5' UTR consists of SEQ ID NOs:2 or 7.

In an embodiment, a nucleic acid construct is provided comprising an ortholog to a chlorophyll binding Ab promoter and 5' UTR. In an embodiment, the chlorophyll binding Ab promoter and 5' UTR is a *Glycine max* chlorophyll binding Ab promoter and 5' UTR. In an embodiment, a nucleic acid construct is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6. In an embodiment, a nucleic acid construct is provided comprising a chlorophyll binding Ab and 5' UTR promoter that is operably linked to a polylinker. In an embodiment, a gene expression cassette is provided comprising a chlorophyll binding Ab promoter and 5' UTR that is operably linked to a non-chlorophyll binding Ab transgene. In one embodiment the promoter and 5' UTR consists of SEQ ID NOs:5 and 10. In an illustrative embodiment, a gene expression cassette comprises a chlorophyll binding Ab promoter and 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an interfering RNA (e.g., an artificial micro RNA, a hairpin RNA, an antisense RNA), or combinations thereof.

```
                                              SEQ ID NO:5
CTTCATATAAATGTATTTCAAAAGTATTTCTTCTAGAATAAACTAAAGCT

ATTACAGATGAAAAATTCTTAAAAAATTATTTGACCTTCATATATGGGTC

CTTTTCTAATTAATAATTAACTATATAGGTGCATTCTAAATGCTCCTATA

TTATCTGCTTTCTCCTCTTCTTTCCTTTTTTCCTAGTCGCTCACGAAAAT

CTCCTATAATCCTCTGCAGTTTTCGAAATCAATAACCGACTCCTAGAACC

TGTCCATGTCTAACTTAATAAATCGTGAGGGTGTGATTGTGATTACTTTG

AATCTTTAATTTTTGACATTAAAACAAGACCAAACAAAAACCTTCAGGTT

ACGTGAGACTCCAACCTACCCAAGTTATGTATTAGTTTTTCCTGGTCCAG

AAGAAAAGAGCCATGCATTAGTTTATTACAACTAACTATATTTCAATTTC

ATGTAAGTGTGCCCCCTCATTAAAATCGACCTGTGTAACCATCAACCTGT

AGTTCGCTCTTTTCACCATTTGTCTCTCTGTCTTTATCTTCCCTCCCCCA

TTGCCAATATTTGTTGCAATACAACATCTCTCCGTTGCAATCACTCATTT

CAAATTTTGTGGTTCTCATTTGCCCTAGTACAACATTAGATGTGGACCCA

AAAATATCTCACATTGAAAGCATATCAGTCACACAATTCAATCAATTTTT

TCCACATCACCTCCTAAATTGAATAACATGAGAAAAAAATAGCTAAGTGC

ACATACATATCTACTGGAATCCCATAGTCCTACGTGGAAGACCCACATTG

GCCACAAAACCATACGAAGAATCTAACCCATTTAGTGGATTATGGGGGTG
```

```
                                                -continued
CCAAGTGTACCAAACAAAATCTCAAACCCCCAATGAGATTGTAGCAATAG

ATAGCCCAAGATAAGAACCCAACCCACTTCAACCCCATATAAATAAACCCG

GACACAACTTCACCAAGTCACTCACCACTTCAAAACACTCATAACACAAA

GCACAAAGCAAAGCTCATCCTTGAGTTAAAAAA GmCAB promoter and 5'UTR. The 5'UTR sequence is bolded.
                                                SEQ ID NO: 10
AGGGGGTACACTTTACATAATTGTATTTCAAAAGTATTTCTTCAAGAGTA

AACAAAAGCTAGCACAGATGAAAAAACATTTTAAAAAAATTATTTGACCT

TCATGTACGAGTGCTTTCTAAATTAAATAATTGACTGTATAGAGGTGCCT

TCTAAATTCTCCTATATTATTTCAGCTTGCTTTCTTTCTTATTTTCCCCA

GTCGCTCACGAAAATCTCCTATTCTAATATCTTGTGCAGTTTTGGCAATC

AACATGTATTAGTGAGGGTGTGACTGTGATTACTTTGATTTTTGAAACTA

AAACAATACCAAACAAAAACCCTCTGGTAACGTGAAGTAATAGTTTTTTT

GGTACTGAAAGAAAAAAGATAGCCATGTATTTATTTAGTTTATTACAACT

AACTATATTTCAATTTGATGTAAGTGCCCCCTCATTAAAATGGACCTGTG

TAACCATCAACCTCTAGTTCGCTCTTTTCACCATTTGTCTCTCTGTCTCT

GACTTGGCAATATTTGAAATTTTGTGGTTCTCATTTCCCTTAGTACAACA

CCAGATGTGGACCCAAAAATATCTCAGACATTGAAACTAAGGATAGCCAC

ATAATTCAAGCCATTTTCCACGTCACCTCCTCAATGGAATAGCATAAGAA

AATAAGTTAACAAACATATCTACTGGAATCCCATAGTCCTACGTGGAAGA

CCCACATTGGTCAGAAAAGCAGAGAAAGAATCTAACCCATTTAGTGGATT

ATAGGGGTGCCAAGTGTACCAAACAAAATCTGAAAGCCCCAATGAGATAG

TAGCAATAGATAGGCCAAGATAAGAACCCCAACCACTTGAAGCCCATATA

AATAAACCCCCACACAACTTCACTGAATCACTCACAACTCCATAACACAA

GGCAGAAAGCAAGCTCATCCTAGAGTTTTAAAA is promoter and

5'UTR for Glyma05g25810..5'UTR sequence is bolded.
```

In an embodiment, a gene expression cassette comprises a chlorophyll binding Ab 5' UTR that is operably linked to a promoter, wherein the promoter is a *Glycine max* chlorophyll binding Ab promoter, a virus (e.g., Cassava vein mosaic virus promoter) or a bacteria (e.g., *Agrobacterium tumefaciens* delta mas), or other promoter that originates from a plant (e.g., *Arabidopsis* Ubiquitin3, Ubiquitin10, Ubiquitin11, Ubiquitin14 genes, *Arabidopsis* actin2 gene, etc.). In an illustrative embodiment, a gene expression cassette comprises a *Glycine max* chlorophyll binding Ab 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, an interfering RNA (e.g., an artificial micro RNA, a hairpin RNA, or an antisense RNA), a selectable marker transgene, or combinations thereof.

In an embodiment a nucleic acid construct is provided comprising a promoter and a optionally a polylinker and one or more of the following elements:

a) a 5' untranslated region;

b) a 3' untranslated region (with or without an intron), which may further be included within a terminator wherein the promoter comprises SEQ ID NOs:1, 6, or a sequence having 95% or 98% sequence identity with SEQ ID NOs:1 or 6;

the 5' untranslated region comprises SEQ ID NOs:2, 7, or a sequence having 95% or 98% sequence identity with SEQ ID NOs:2 or 7 (e.g., the promoter and 5' untranslated region comprise SEQ ID NOs:5 or 10);

the 3' untranslated region comprises SEQ ID NOs:3, 8, or a sequence having 95% or 98% sequence identity with SEQ ID NOs:3 or 8; further wherein said promoter is operably linked to each optional element, when present.

In one embodiment a nucleic acid construct is provided comprising a promoter and a non-chlorophyll binding Ab transgene and optionally one or more of the following elements:

a) a 5' untranslated region;

b) a 3' untranslated region, wherein the promoter comprises SEQ ID NOs:1, 6, or a sequence having 95% or 98% sequence identity with SEQ ID NOs:1 or 6;

the 5' untranslated region comprises SEQ ID NOs:2, 7, or a sequence having 95% or 98% sequence identity with SEQ ID NOs:2 or 7 (e.g., the promoter and 5' untranslated region comprise SEQ ID NOs:5 or 10);

the 3' untranslated region comprises SEQ ID NOs:3, 8, or a sequence having 95% or 98% sequence identity with SEQ ID NOs:3 or 8; further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In an embodiment, a gene expression cassette comprises a promoter (SEQ ID NOs:1 or 6) operably linked to a 5' UTR (SEQ ID NOs:2 or 7) and 3' UTR (SEQ ID NOs:3 or 8).

In an embodiment, a gene expression cassette comprises a chlorophyll binding Ab promoter, a chlorophyll binding Ab 5' UTR, and a chlorophyll binding Ab 3' UTR. In an embodiment, a chlorophyll binding Ab promoter, a chlorophyll binding Ab 5' UTR, and a chlorophyll binding Ab transcription terminator fragment containing a 3' UTR can each be independently a *Glycine max* chlorophyll binding Ab promoter and a *Glycine max* chlorophyll binding Ab 3' UTR. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6; b) a transcription termination fragment, wherein the transcription terminator fragment containing 3' UTR is at least 80%, 85%, 90%, 91%, 92%, 93%, 94%, 95%, 96%, 97%, 98%, 99%, 99.5%, 99.8%, or 100% identical to SEQ ID NOs:4 or 9; c) a 5' UTR, wherein the 5' UTR is at least 80%, 85%, 90%, 91%, 92%, 93%, 94%, 95%, 96%, 97%, 98%, 99%, 99.5%, 99.8%, or 100% identical to SEQ ID NOs:2 or 7.

For example, a gene expression cassette may include a promoter and a 5' UTR wherein the promoter is a polynucleotide of SEQ ID NOs:1 or 6 and the 5' UTR is a polynucleotide of SEQ IDNOs:2 or 7.

For example, a gene expression cassette may include a promoter, an intron, a 5' UTR, and a transcription terminator fragment containing a 3' UTR wherein the promoter is a polynucleotide of SEQ ID NOs:1 or 6, the 5' UTR is a polynucleotide of SEQ ID NOs:2 or 7, and the transcription terminator fragment containing a 3' UTR and is a polynucleotide of SEQ ID NOs:4 or 9.

In addition, a gene expression cassette may include both a promoter and a transcription terminator fragment containing a 3' UTR wherein the promoter is a polynucleotide of SEQ ID NOs:1 or 6 and a transcription terminator fragment containing a 3' UTR of SEQ ID NOs:4 or 9.

In an embodiment, a gene expression cassette comprises a chlorophyll binding Ab promoter, chlorophyll binding Ab 5' UTR, and a chlorophyll binding Ab transcription terminator fragment containing 3' UTR, that are operably linked to a non-chlorophyll binding Ab transgene.

A promoter, an intron, a 5' UTR, and a transcription terminator fragment containing 3' UTR can be operably linked to different transgenes within a gene expression cassette when a gene expression cassette includes one or more transgenes. In an illustrative embodiment, a gene expression cassette comprises a chlorophyll binding Ab promoter and 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an interfering RNA (e.g., an artificial micro RNA, a hairpin RNA, or an antisense RNA), or combinations thereof. In an illustrative embodiment, a gene expression cassette comprises a chlorophyll binding Ab promoter and 5' UTR, and a 3' UTR that are operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an interfering RNA (e.g., an artificial micro RNA, a hairpin RNA, or an antisense RNA), or combinations thereof. In an illustrative embodiment, a gene expression cassette comprises a chlorophyll binding Ab transcription terminator fragment containing 3' UTR that is operably linked to a transgene, wherein the transgene encodes for a gene product that enhances insecticidal resistance, herbicide tolerance, nitrogen use efficiency, water use efficiency, nutritional quality, an artificial micro RNA, a hairpin RNA, an antisense RNA, or combinations thereof.

A chlorophyll binding Ab 5' UTR can be operably linked to different promoters within a gene expression cassette. In an illustrative embodiment, the promoters originate from a plant (e.g., *Glycine max* chlorophyll binding Ab promoter and 5' UTR), a virus (e.g., Cassava vein mosaic virus promoter), or a bacteria (e.g., *Agrobacterium tumefaciens* delta mas). In an illustrative embodiment, a gene expression cassette comprises a chlorophyll binding Ab promoter and 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an interfering RNA (e.g., an artificial micro RNA, a hairpin RNA, or an antisense RNA), or combinations thereof.

In an embodiment, a vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

In accordance with one embodiment a nucleic acid vector is provided comprising a recombinant gene expression cassette wherein the recombinant gene expression cassette comprises a chlorophyll binding Ab-based promoter operably linked to a polylinker sequence, a non-chlorophyll binding Ab transgene or combination thereof. In one embodiment the recombinant gene cassette comprises a chlorophyll binding Ab-based promoter operably linked to a non-chlorophyll binding Ab transgene. In one embodiment the recombinant gene cassette comprises a chlorophyll binding Ab-based promoter as disclosed herein operably linked to a polylinker sequence. The polylinker is operably linked to the chlorophyll binding Ab-based promoter in a manner such that insertion of a coding sequence into one of the restriction sites of the polylinker will operably link the coding sequence allowing for expression of the coding sequence when the vector is transfected into a host cell.

In accordance with one embodiment the chlorophyll binding Ab-based promoter comprises SEQ ID NOs:1, 6, or a sequence that has 90, 95, 98 or 99% sequence identity with SEQ ID NOs:1 or 6. In accordance with one embodiment the chlorophyll binding Ab based promoter consists of SEQ ID NO:1 or a 910 bp sequence that has 90, 95, 98 or 99% sequence identity with SEQ ID NO:1. In accordance with a further embodiment the chlorophyll binding Ab based promoter consists of SEQ ID NO:6 or a 818 bp sequence that has 90, 95, 98 or 99% sequence identity with SEQ ID NO:6.

In accordance with one embodiment the 3' untranslated region comprises SEQ ID NOs:3, 8, or a sequence that has 90, 95, 98, 99 or 100% sequence identity with SEQ ID NOs:3 or 8. In a further embodiment the 3' untranslated region consists of SEQ ID NO:3 or a 465 bp sequence that has 90, 95, 98 or 99% sequence identity with SEQ ID NO:3. In a further embodiment the 3' untranslated region consists of SEQ ID NO:8 or a 296 bp sequence that has 90, 95, 98 or 99% sequence identity with SEQ ID NO:8.

In accordance with one embodiment, the transcription terminator fragment containing 3' UTR sequence comprises SEQ ID NOs:4, 9, or a sequence that has 90, 95, 98, 99 or 100% sequence identity with SEQ ID NOs:4 or 9. In a further embodiment the transcription terminator fragment containing 3' UTR consists of SEQ ID NO:4 or a 556 bp sequence that has 90, 95, 98, or 99% sequence identity with SEQ ID NO:4. In a further embodiment the transcription terminator fragment containing 3' UTR sequence consists of SEQ ID NO:9 or a 543 bp sequence that has 90, 95, 98, or 99% sequence identity with SEQ ID NO:9.

In accordance with one embodiment the nucleic acid vector further comprises a sequence encoding a selectable marker. In accordance with another embodiment the recombinant gene cassette is operably linked to an *Agrobacterium* T-DNA border. In accordance with one embodiment the recombinant gene cassette further comprises a first and second T-DNA border, wherein a first T-DNA border is operably linked to one end of the gene construct, and said second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NOs:5, 10-11, or a sequence having 90, 95, 98 or 99% sequence identity with SEQ ID NOs:5 or 10-11.

Transgenes of interest and suitable for use in the present disclosed constructs include, but are not limited to, coding sequences that (1) confer resistance to pests or disease, (2) confer tolerance to herbicides, (3) value added traits, and (4) downregulate expression of native genes or transgenes. In accordance with one embodiment the transgene encodes a selectable marker or a gene product conferring insecticidal resistance, herbicide tolerance, nitrogen use efficiency, water use efficiency, an interfering RNA, or nutritional quality.

In accordance with one embodiment a nucleic acid vector is provided comprising a gene cassette wherein the gene cassette comprises a promoter region operably linked to the 5' end of a transgene wherein the 3' end of the transgene is linked to a 3' untranslated region. In one embodiment the promoter region comprises SEQ ID NOs:1, 6, or a sequence that has 90, 95, 98 or 99% sequence identity with SEQ ID NOs:1 or 6. In accordance with one embodiment the promoter region consists of SEQ ID NOs:1 or 6. In one embodiment the 3' untranslated region comprises SEQ ID NOs:3, 8, or a sequence that has 90, 95, 98 or 99% sequence identity with SEQ ID NOs:3 or 8, and in one embodiment the 3' untranslated region consists of SEQ ID NO:3 or a 465 bp sequence having 90, 95, 98 or 99% sequence identity with SEQ ID NO:3. In one embodiment the 3' untranslated region consists of SEQ ID NO:8 or a 296 bp sequence having 90, 95, 98 or 99% sequence identity with SEQ ID NO:8.

In accordance with one embodiment a nucleic acid vector is provided comprising a gene cassette wherein the gene cassette comprises a promoter region operably linked to the 5' end of a 5' untranslated region, wherein the 3' end of the 5' untranslated region is operably linked to the 5' end of the transgene wherein the 3' end of the transgene is linked to a 3' untranslated region. In one embodiment the promoter region comprises or consists of SEQ ID NO:1 or a sequence that has 90, 95, 98 or 99% sequence identity with SEQ ID NO:1. In one embodiment the promoter region consists of SEQ ID NO:1 or a 910 bp sequence that has 90, 95, 98 or 99% sequence identity with SEQ ID NO:1. In one embodiment the promoter region comprises or consists of SEQ ID NO:6 or a sequence that has 90, 95, 98 or 99% sequence identity with SEQ ID NO:6. In one embodiment the promoter region comprises or consists of SEQ ID NO:6 or a 818 bp sequence that has 90, 95, 98 or 99% sequence identity with SEQ ID NO:6. In accordance with one embodiment the 5' untranslated region comprises or consists of SEQ ID NOs:2, 7 or a sequence that has 90, 95, 98 or 99% sequence identity with SEQ ID NOs:2 or 7. In one embodiment the 5' untranslated region consists of SEQ ID NO:2 or a 123 bp sequence that has 90, 95, 98 or 99% sequence identity with SEQ ID NO:2. In one embodiment the 5' untranslated region consists of SEQ ID NO:7 or a 115 bp sequence that has 90, 95, 98 or 99% sequence identity with SEQ ID NO:7. In a further embodiment the nucleic acid vector further comprises a chlorophyll binding Ab 3' untranslated region and the transgene, and operably linked to the promoter and transgene.

In an embodiment, a cell or plant is provided comprising a gene expression cassette as disclosed herein. In an embodiment, a cell or plant comprises a vector comprising a gene expression cassette as disclosed herein. In an embodiment, a vector can be a plasmid, a cosmid, a bacterial artificial chromosome (BAC), a bacteriophage, or a virus. Thereby, a cell or plant comprising a gene expression cassette as disclosed herein is a transgenic cell or transgenic plant, respectively. In an embodiment, a transgenic plant can be a dicotyledonous plant. In an embodiment, a transgenic dicotyledonous plant can be, but is not limited to tomato, tobacco, potato, Arabidopsis, soybean, cotton, sunflower, and canola. In an embodiment, a transgenic plant can be a monocotyledonous plant. In an embodiment, a transgenic mononocotyledonous plant can be, but is not limited to maize, wheat, rice, sorghum, oats, rye, bananas, sugar cane, turf grass, and millet. An embodiment also includes a transgenic seed from a transgenic plant as disclosed herein.

In an embodiment, a gene expression cassette includes two or more transgenes. The two or more transgenes may not be operably linked to a promoter, intron, 5' UTR, or transcription terminator fragment containing 3' UTR and an intron as disclosed herein. In an embodiment, a gene expression cassette includes one or more transgenes. In an embodiment with one or more transgenes, at least one transgene is operably linked to a promoter, 5' UTR, or transcription terminator fragment containing 3' UTR.

Transgenes

Various selectable markers also described as reporter genes can be incorporated into a chosen expression vector to allow for identification and selection of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring tolerance to herbicidal compounds.

Herbicide tolerance genes can be utilized as selectable markers or to confer a desired herbicide tolerance phenotype to the plant and generally code for a modified target protein insensitive to the herbicide or for an enzyme that degrades or detoxifies the herbicide in the plant before it can act. For example, tolerance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1, or an aad-12 gene, which detoxifies the respective herbicides.

In an embodiment, herbicides which can inhibit normal plant growth and development, including, but not limited to, acetohydroxyacid synthase (AHAS) inhibitors, such as imidazolinones, triazolopyrimidines, pyrimidinyl(thio)benzoates, sulfonylureas, and sulfonylaminocarbonyltriazolinones; synthetic auxins, such as phenoxy carboxylic acids (e.g., 2,4-D), benzoic acids (e.g., dicamba), pyridine carboxylic acids, quinoline carboxylic acids, arylpicolinates; acetyl CoA carboxylase (ACCase) inhibitors, such as aryloxyphenoxypropionates, cyclohexanediones, and phenylpyrazolines; 5-enolpyruvylshikimate-3-phosphate (EPSP) synthase inhibitors, such as glyphosate; glutamine synthetase inhibitors, such as glufosinate and phosphinothricin; carotenoid biosynthesis inhibitors, such as triazoles; phytoene desaturase (PDS) inhibitors, such as pyridazinones, pyridinecarboxamides, isoxazolidinones, and others; 4-hydroxyphenyl-pyruvatedioxygenase (HPPD) inhibitors, such as triketones, isoxazoles, pyrazoles, and others; protoporphyrinogen oxidase (PPO) inhibitors, such as diphenylethers, phenylpyrazoles, N-phenylphthalimides, thiadiazoles, oxadiazoles, triazolinones, pyrimidindiones, and others; dihydropteroate (DHP) synthase inhibitors, such as carbamates; cellulose biosynthesis inhibitors, such as nitriles, benzamides, and triazolocarboxamides; microtubule assembly inhibitors, such as dinitroanilines, phosphoroamidates, pyridines, benzamides, and others; mitosis inhibitors, such as carbamates; photosynthesis (PS) inhibitors, such as triazines, triazinones, triazolinones, uracils, ureas, phenylcarbamates, phenylpyridizines, nitriles, benzothiadiazinones, amides, pyridazinones, and bipyridyliums; lipid biosynthesis inhibitors, such as thiocarbamates, phosphorodithioates, and benzofurans; very long chain fatty acid (VLCFA) inhibitors, such as chloroacetamides, acetamides, oxyacetamides, tetrazolinones, and others (e.g., cafenstrole); auxin transport inhibitors, such as phthalamates and semicarbazones; and membrane disruptors, such as dinitrophenols. Genes conferring tolerance to many of these herbicides are well known as sources of target-site-based and non-target-site-based herbicide tolerance.

Genes for tolerance of plants to acetohydroxyacid synthase (AHAS) or acetolactate synthase (ALS) inhibitors, synthetic auxins, and acetyl CoA carboxylase (ACCase) inhibitor herbicides are well known. Glyphosate tolerance genes include mutant 5-enolpyruvylshikimate-3-phosphate synthase (EPSPS) and dgt genes (via the introduction of recombinant nucleic acids and/or various forms of in vivo mutagenesis of native EPSPS genes), aroA genes and glyphosate acetyl transferase (GAT) genes, respectively. Resistance genes for other phosphono compounds include bar and DSM2 genes from *Streptomyces* species, including *Streptomyces hygroscopicus*, *Streptomyces viridichromogenes*, and *Sterpomyces coelicolor*. Exemplary genes conferring tolerance to pyridinoxy, phenoxy propionic acids, cyclohexanediones and/or aryloxyphenoxypropanoic acid (including Haloxyfop, Diclofop, Fenoxyprop, Fluazifop, Quizalofop) include genes of AAD-1, AAD-12 and acetyl coenzyme A carboxylase (ACCase)—Acc1-S1, Acc1-S2 and Acc1-S3 (ACCase inhibitor-encoding genes), and detoxification genes. In an embodiment, herbicides can inhibit photosynthesis, including triazine (psbA and 1s+ genes), triazinones, triazolinones, uracils, ureas, phenylcarbamates, nitriles, phenylpyridizines, benzothiadiazinones, amides, pyridazinones, benzonitrile (nitrilase gene), or bipyridyliums.

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; dsm2; aad12; aad1; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166,302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment. Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp. NGR234, *Sinorhizoboium meliloti*, *Mesorhizobium loti*, potato virus X, cauliflower mosaic virus, cassava vein mosaic virus, and/or tobacco mosaic virus.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soybean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and northern blotting and PCR; biochemical assays, such as detecting the presence of a protein product, e.g., by immunological means (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described, and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

If desired exact genomic location can be determined using PCR or by genome wide Next generation sequencing technologies. Expression of transgenes can also be assayed using mRNA abundances. Epigenetic characteristics of transgenes such as DNA methylation and presence of transgene specific small RNAs may be determined using specialized genome wide methods.

Method of Expressing a Transgene

In an embodiment, a method of expressing at least one transgene in a plant comprises growing a plant comprising a chlorophyll binding Ab promoter operably linked to at least one transgene. In an embodiment, a method of expressing at least one transgene in a plant comprises growing a plant comprising a chlorophyll binding Ab 5' UTR operably linked to at least one transgene. In an embodiment, a method of expressing at least one transgene in a plant comprises growing a plant comprising a chlorophyll binding Ab promoter and a chlorophyll binding Ab 5' UTR operably linked to at least one transgene. In an embodiment, a method of expressing at least one transgene in a plant comprises growing a plant comprising a chlorophyll binding Ab transcription terminator fragment containing 3' UTR operably linked to at least one transgene. In an embodiment, a method of expressing at least one transgene in a plant tissue or plant cell comprises culturing a plant tissue or plant cell comprising a chlorophyll binding Ab promoter operably linked to at least one transgene. In an embodiment, a method of expressing at least one transgene in a plant tissue or plant cell comprises culturing a plant tissue or plant cell comprising a chlorophyll binding Ab 5' UTR operably linked to at least one transgene. In an embodiment, a method of expressing at least one transgene in a plant tissue or plant cell comprises culturing a plant tissue or plant cell comprising a chlorophyll binding Ab promoter and a chlorophyll binding Ab 5' UTR operably linked to at least one transgene. In an embodiment, a method of expressing at least one transgene in a plant tissue or plant cell comprises culturing a plant tissue or plant cell comprising a chlorophyll binding Ab transcription terminator fragment containing a 3' UTR operably linked to at least one transgene.

In an embodiment, a method of expressing at least one transgene in a plant comprises growing a plant comprising a gene expression cassette comprising a chlorophyll binding Ab promoter and chlorophyll binding Ab 5' UTR operably linked to at least one transgene. In one embodiment the chlorophyll binding Ab promoter and chlorophyll binding Ab 5' UTR consists of a sequence selected from SEQ ID NOs:5, 10, 11, or a sequence that has 90, 95, 98 or 99% sequence identity with a sequence selected from SEQ ID NOs:5, 10, or 11. In an embodiment, a method of expressing at least one transgene in a plant comprises growing a plant comprising a gene expression cassette comprising a chlorophyll binding Ab 5' UTR operably linked to at least one transgene. In an embodiment, a method of expressing at least one transgene in a plant comprises growing a plant comprising a gene expression cassette comprising a chlorophyll binding Ab promoter operably linked to at least one transgene. In an embodiment, a method of expressing at least one transgene in a plant comprises growing a plant comprising a gene expression cassette comprising a chlorophyll binding Ab transcription terminator fragment containing 3' UTR operably linked to at least one transgene. In an embodiment, a method of expressing at least one transgene in a plant tissue or plant cell comprises culturing a plant tissue or plant cell comprising a gene expression cassette a chlorophyll binding Ab promoter and 5' UTR operably linked to at least one transgene. In an embodiment, a method of expressing at least one transgene in a plant tissue or plant cell comprises culturing a plant tissue or plant cell comprising a gene expression cassette a chlorophyll binding Ab 5' UTR operably linked to at least one transgene. In an embodiment, a method of expressing at least one transgene in a plant tissue or plant cell comprises culturing a plant tissue or plant cell comprising a gene expression cassette a chlorophyll binding Ab promoter and a chlorophyll binding Ab 5' UTR operably linked to at least one transgene. In an embodiment, a method of expressing at least one transgene in a plant tissue or plant cell comprises culturing a plant tissue or plant cell comprising a gene expression cassette comprising a chlorophyll binding Ab transcription terminator fragment containing 3' UTR operably linked to at least one transgene.

Transgenic Plants

In an embodiment, a plant, plant tissue, or plant cell comprises a chlorophyll binding Ab promoter. In an embodiment, a chlorophyll binding Ab promoter can be a *Glycine max* chlorophyll binding Ab promoter. In an embodiment, a plant, plant tissue, or plant cell comprises a gene expression cassette comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6 wherein the promoter is operably linked to a non-chlorophyll binding Ab transgene. In an embodiment, a plant, plant tissue, or plant cell comprises a gene expression cassette comprising a sequence selected from SEQ ID NOs:1, 6, or a sequence that has 90, 95, 98 or 99% sequence identity with a sequence selected from SEQ ID NOs:1 or 6 that is operably linked to a non-chlorophyll binding Ab transgene. In an illustrative embodiment, a plant, plant tissue, or plant cell comprises a gene expression cassette comprising a chlorophyll binding Ab promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an artificial micro RNA, a hairpin RNA, an antisense RNA, or combinations thereof.

In an embodiment, a plant, plant tissue, or plant cell comprises a gene expression cassette comprising a 3' UTR. In an embodiment, a plant, plant tissue, or plant cell comprises a gene expression cassette comprising a chlorophyll binding Ab 3' UTR. In an embodiment, the chlorophyll binding Ab transcription terminator fragment containing a 3' UTR is a *Glycine max* chlorophyll binding Ab 3' UTR.

In an embodiment, a plant, plant tissue, or plant cell comprises a gene expression cassette comprising a 5' UTR, wherein the 5' UTR is at least 80%, 85%, 90%, 91%, 92%, 93%, 94%, 95%, 96%, 97%, 98%, 99%, 99.5%, 99.8%, or 100% identical to SEQ ID NOs:2 or 7. In an embodiment, a plant, plant tissue, or plant cell comprises a gene expression cassette comprising a chlorophyll binding Ab 5' UTR that is operably linked to a transgene. In an illustrative embodiment, a plant, plant tissue, or plant cell comprising a gene expression cassette comprising a chlorophyll binding Ab 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an artificial micro RNA, a hairpin RNA, an antisense RNA, or combinations thereof.

In an embodiment, a plant, plant tissue, or plant cell comprises a gene expression cassette comprising a chlorophyll binding Ab promoter and a chlorophyll binding Ab 3' UTR. In an embodiment, a plant, plant tissue, or plant cell comprises a chlorophyll binding Ab promoter, transcription terminator fragment containing 3' UTR can each be independently a *Glycine max* chlorophyll binding Ab promoter and a *Glycine max* chlorophyll binding Ab 3' UTR. In an embodiment, a plant, plant tissue, or plant cell comprises a gene expression cassette comprising a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NOs:1 or 6 and b) a 3' UTR, wherein the transcription terminator fragment containing 3' UTR is at least 80%, 85%, 90%, 91%, 92%, 93%, 94%, 95%, 96%, 97%, 98%, 99%, 99.5%, 99.8%, or 100% identical to SEQ ID NOs:4 or 9.

In an embodiment, a plant, plant tissue, or plant cell comprises a gene expression cassette comprising a chlorophyll binding Ab promoter, chlorophyll binding Ab 5' UTR, and a chlorophyll binding Ab transcription terminator fragment containing 3' UTR, that are operably linked to a transgene. The promoter, 5' UTR, and transcription terminator fragment containing 3' UTR can be operably linked to different transgenes within a gene expression cassette when a gene expression cassette includes two or more transgenes. In an illustrative embodiment, a gene expression cassette comprises a chlorophyll binding Ab promoter and 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an artificial micro RNA, a hairpin RNA, an antisense RNA, or combinations thereof.

In an illustrative embodiment, a gene expression cassette comprises a chlorophyll binding Ab 5' UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, an artificial micro RNA, a hairpin RNA, an antisense RNA, or combinations thereof. In an embodiment, a gene expression cassette comprises a chlorophyll binding Ab 5' UTR that is operably linked to a promoter, wherein the promoter is a *Glycine max* chlorophyll binding Ab promoter, or a promoter that originates from a plant (e.g., *Glycine max* chlorophyll binding Ab promoter), a virus (e.g., Cassava vein mosaic virus promoter) or a bacteria (e.g., *Agrobacterium tumefaciens* delta mas). In an illustrative embodiment, a gene expression cassette comprises a chlorophyll binding Ab transcription terminator fragment containing 3' UTR that is operably linked to a transgene, wherein the transcription terminator fragment containing 3' UTR can be an insecticidal resistance transgene, an herbicide tolerance transgene, a nitrogen use efficiency transgene, a water use efficiency transgene, a nutritional quality transgene, a DNA binding transgene, a selectable marker transgene, an iRNA, or combinations thereof.

In an embodiment, a plant, plant tissue, or plant cell comprises a vector comprising a chlorophyll binding Ab promoter, 5' UTR, and/or transcription terminator fragment containing 3' UTR as disclosed herein. In an embodiment, a plant, plant tissue, or plant cell comprises a vector comprising a chlorophyll binding Ab promoter, 5' UTR, and/or transcription terminator fragment containing 3' UTR as disclosed herein operably linked to a non-chlorophyll binding Ab transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus.

In accordance with one embodiment a plant, plant tissue, or plant cell is provided wherein the plant, plant tissue, or plant cell comprises a non-endogenous chlorophyll binding Ab derived promoter and 5' UTR sequence operably linked to a transgene, wherein the chlorophyll binding Ab derived promoter and 5' UTR sequence comprises a sequence SEQ ID NOs:5, 10, or a sequence having 90, 95, 98 or 99% sequence identity with SEQ ID NOs:5 or 10. In one embodiment a plant, plant tissue, or plant cell is provided wherein the plant, plant tissue, or plant cell comprises SEQ ID NOs:1, 5, 6, 10-11, or a sequence that has 90% sequence identity with SEQ ID NOs:1, 5, 6, or 10-11 operably linked to a non-chlorophyll binding Ab transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, sorghum, oats, rye, bananas, turf grass, sugar cane, soybean, cotton, sunflower, tobacco, potato, tomato, *Arabidopsis*, and canola. In one embodiment the plant is *Glycine max*. In accordance with one embodiment the plant, plant tissue, or plant cell comprises SEQ ID NOs:1, 5, 6, 10-11 or a sequence having 90, 95, 98 or 99% sequence identity with SEQ ID NOs:1, 5, 6, 10-11 or operably linked to a non-chlorophyll binding Ab transgene. In one embodiment the plant, plant tissue, or plant cell comprises a promoter operably linked to a transgene wherein the promoter consists of SEQ ID NOs:1, 6, or a sequence having 90, 95, 98 or 99% sequence identity with SEQ ID NOs:1 or 6. In accordance with one embodiment the gene construct comprising non-endogenous chlorophyll binding Ab derived promoter sequence operably linked to a transgene is incorporated into the genome of the plant, plant tissue, or plant cell.

In one embodiment a non-Glycine plant, plant tissue, or plant cell is provided comprising SEQ ID NOs:1, 5, 6, 10-11, or a sequence that has 90, 95, 98 or 99% sequence identity with SEQ ID NOs:1, 5, 6, 10-11, operably linked to a transgene. In accordance with one embodiment the non-Glycine plant, plant tissue, or plant cell is a dicotyledonous or monocotyledonous plant or plant cell or tissue derived from a dicotyledonous or monocotyledonous plant. In one embodiment the plant is selected from the group consisting of maize, wheat, rice, sorghum, oats, rye, turf grass, bananas, sugar cane, soybean, cotton, tobacco, potato, tomato, *Arabidopsis*, sunflower, and canola. In accordance with one embodiment the promoter sequence operably linked to a transgene is incorporated into the genome of the plant, plant tissue, or plant cell. In one embodiment the plant, plant tissue, or plant cell further comprises a 5' untranslated region comprising SEQ ID NOs:2, 7, or a sequence that has 90% sequence identity with SEQ ID NOs:2 or 7, wherein the 5' untranslated region is inserted between, and operably linked to, said promoter and said transgene.

In one embodiment a non-Glycine plant, plant tissue, or plant cell is provided that comprises SEQ ID NOs:1, 6, or a sequence that has 90, 95, 98 or 99% sequence identity with SEQ ID NOs:1 or 6, operably linked to the 5' end of a transgene comprising SEQ ID NOs:2 or 7, and a 3' untranslated region comprising SEQ ID NOs:3, 8, or a sequence that has 90% sequence identity with SEQ ID NOs:3 or 8, wherein the 3' untranslated region is operably linked to said transgene. In accordance with one embodiment the non-Glycine plant, plant tissue, or plant cell is a dicotyledonous or monocotyledonous plant or is a plant tissue or cell derived from a dicotyledonous or monocotyledonous plant. In one embodiment the plant is selected from the group consisting of maize, wheat, rice, sorghum, oats, rye, bananas, turf grass, sugar cane, soybean, cotton, tobacco, potato, tomato, *Arabidopsis*, sunflower, and canola. In accordance with one embodiment the promoter sequence operably linked to a transgene is incorporated into the genome of the plant, plant tissue, or plant cell. In one embodiment the plant, plant tissue, or plant cell further comprises a 5' untranslated region comprising SEQ ID NOs:2, 7 or a sequence that has 90% sequence identity with SEQ ID NOs:2 or 7, wherein the 5' untranslated region is inserted between, and operably linked to, said promoter and said transgene. In one embodiment the 5' untranslated region consists of SEQ ID NOs:2 or 7.

In one embodiment a non-Glycine plant, plant tissue, or plant cell further comprises a 3' untranslated region of a chlorophyll binding Ab gene of *Glycine max*. In one embodiment the 3' untranslated region comprises or consists of SEQ ID NOs:3, 8, or a sequence that has 90% sequence identity with SEQ ID NOs:3 or 8, wherein the 3' untranslated region is operably linked to 3' end of the transgene.

In an embodiment, a plant, plant tissue, or plant cell according to the methods disclosed herein can be a dicotyledonous plant. The dicotyledonous plant, plant tissue, or plant cell can be, but not limited to tobacco, tomato, *Arabidopsis*, rapeseed, canola, indian mustard, ethiopian mustard, soybean, potato, sunflower, and cotton.

In an embodiment, a plant, plant tissue, or plant cell according to the methods disclosed herein can be a monocotyledonous plant. The monocotyledonous plant, plant tissue, or plant cell can be, but not limited to corn, rice, wheat, sugarcane, barley, rye, sorghum, orchids, bamboo, banana, cattails, lilies, oat, onion, millet, turf grass, and triticale.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or Cl genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) Next Generation Sequencing analysis; 5) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase), EC 2.3.1.183) proteins using an ELISA assay is described in U.S. Patent Publication No. 20090093366 which is herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

While the invention has been described with reference to specific methods and embodiments, it will be appreciated that various modifications and changes may be made without departing from the invention.

EXAMPLES

Example 1

Identification of Soybean Genes with Preferential Expression in Leaves and Sourcing DNA Sequences for the Regulatory Elements from Soybean Genomic Sequence The Glyma08g08770 and Glyma05g25810.1 soybean endogenous genes were identified by analyses of the data in the publically available soybean expression profile (Severin et al, (2010), BMC Plant Biol, 10, 160) as having similar tissue specific expression profiles (FIG. 1A). These two genes have the highest transcript abundance in the young leaves and transcripts were also present in flower and pod tissues. There were low transcript levels in developing seeds and no transcripts were not detected in the roots and nodule. In contrast, high transcript levels for the constitutively expressed genes Glyma20g27950 and Glyma10g39780 were observed in the majority of the tissues (FIG. 1B). Therefore, analysis of the expression pattern for the Glyma08g08770 and Glyma05g25810 showed that these two genes were preferentially expressed in leaves and developing pods. There was little or no detected expression in developing roots and nodule (FIG. 1A). This pattern of expression is of interest for biotechnology as it would provide more differentiated expression pattern for transgenes, where high expression in roots and seeds may not be required.

Based on analysis of protein and DNA sequence similarity, the Glyma08g08770 and Glyma05g25810 are highly similar genes. In many cases, duplicated genes retain similar function and similar expression patterns (FIG. 1A; Guo et al, (2013), PLoS One, 8, e76809; Severin et al, (2010), BMC Plant Biol, 10, 160), as observed for these two genes. The Glyma08g08770 and Glyma05g25810 have high conservation of protein sequences (98% identity) and significant sequence conservation within the non-coding sequences upstream of Glyma08g08770 start codon (73%, FIG. 2) and downstream of the start and stop codon (77%, not shown). Because these genes have similar expression patterns (FIG. 1A), the regulatory elements that specify these expression patterns are also likely to remain conserved and functional in these two paralogous genes. We used the sequence similarity within the non-coding sequences of Glyma08g08770 and Glyma05g25810 to isolate putative upstream and downstream regulatory sequences.

To reduce future possibilities for sequence homology-based small RNA-mediated transgene silencing of the transgenes, we excluded from sourced sequences DNA regions that had similarity to transposable or retro-transposable elements. We also avoided including in the sourced sequence the regions of genomic DNA in which cytosine residues were heavily methylated in any of the sequence contexts (CG, CHG or CHH). This assessment was done using methods as previously disclosed in U.S. Patent Publication No. 20150128309A1, herein incorporated by reference in its entirety.

Figure 2A:
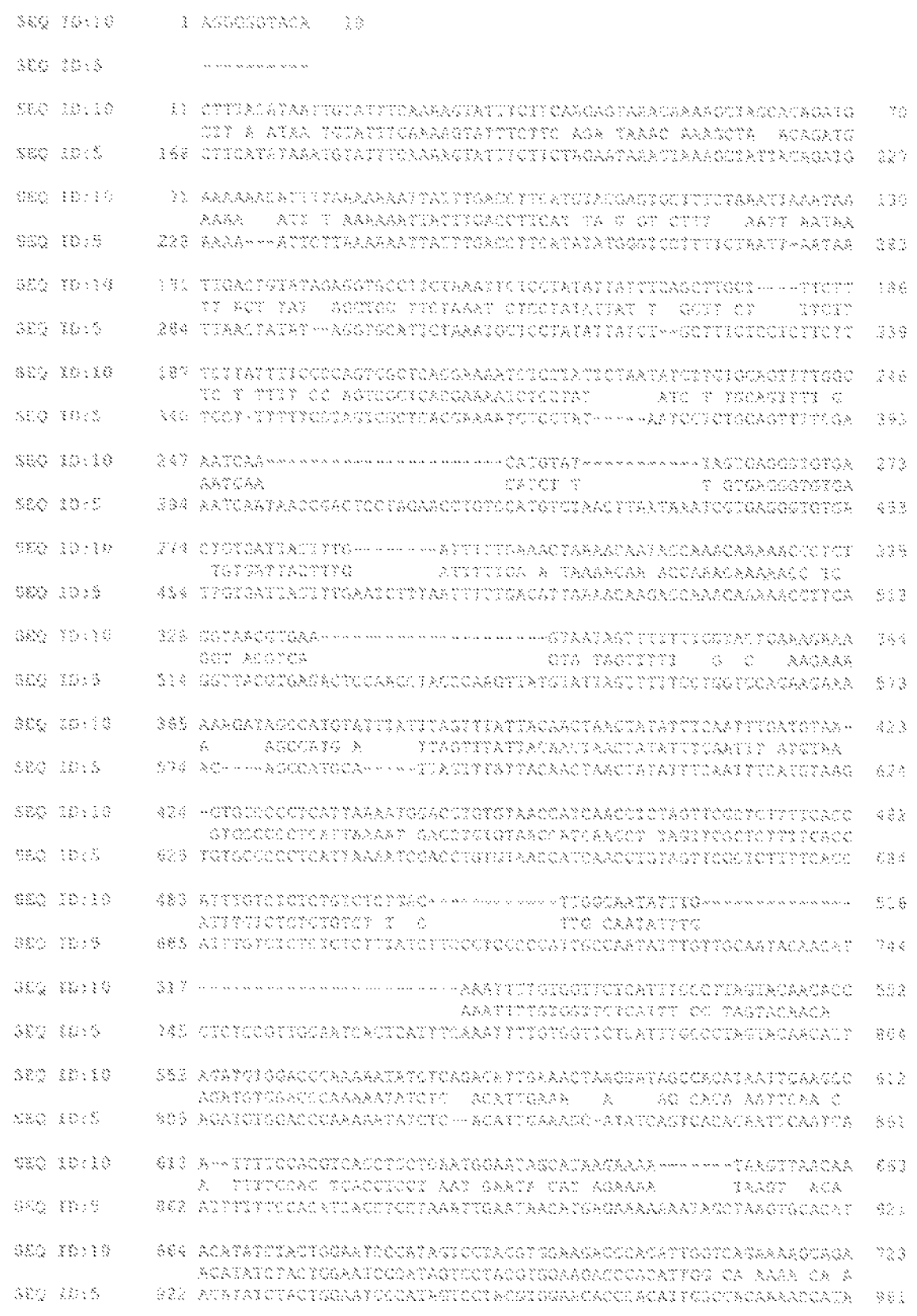
Figure 2B:
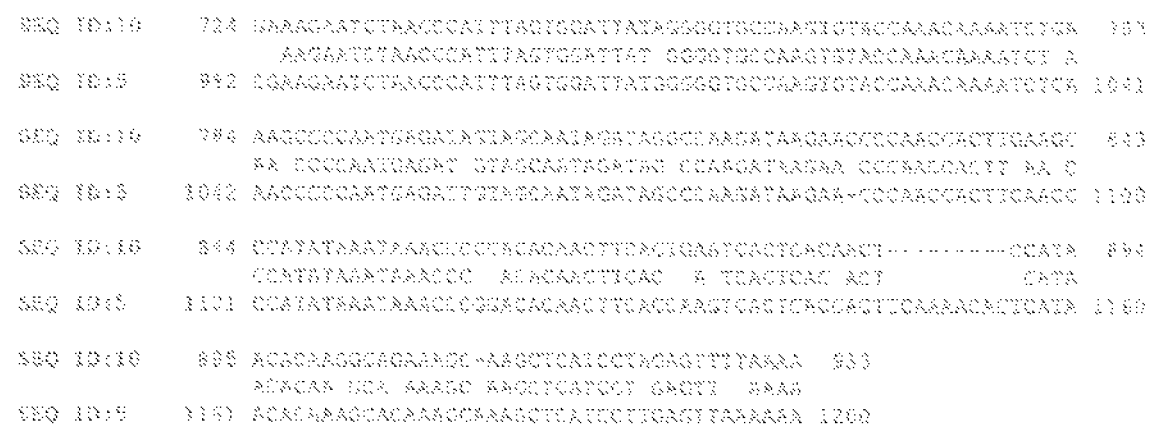

As a result, the sourcing strategy described above lead to the isolation of the 1033 bp fragment from the Glyma08g08770 locus and the 933 bp fragment from the Glyma05g25810 locus. These fragments contained the upstream regulatory sequences from the putative promoters and 5' UTRs. Alignment for the upstream regulatory sequences Glyma08g08770 (SEQ ID NO:5) and Glyma05g25810 (SEQ ID NO:10) is shown in FIG. 2. The upstream regulatory sequences of SEQ ID NO:5 and SEQ ID NO:10 share ~73% sequence identity.

Downstream regulatory sequences play a critical role in gene expression through insuring the proper transcription termination, transcript release from Pol-II RNA polymerase and transcript polyadenylation. RNA polymerase II (Pol-II) has unstructured transcriptional terminators with multiple major and minor polyadenylation sites that may be present within a terminator (Xing et al, (2010), Plant Biotechnol J, 8, 772-782). Because exact poly-adenylation sites within the examined genes were not precisely mapped, we sourced larger terminator fragments, which are at least 100, 200, 300 or more basepairs longer than the most distant annotated poly-adenylation site. Based on this strategy the transcriptional terminator fragment for Glyma08g08770 was extracted from genomic DNA and is shown as SEQ ID NO:4. Sequence of 3' UTR is bolded. Similar strategy was used to source terminator fragment from the Glyma05g25810 gene and it is shown as SEQ ID NO:9.

In addition to the described above identification of GmCAB regulatory sequences, three other soybean genes were identified and candidate regulatory sequences were isolated using methods similar to those described for GmCAB bioinformatic analyses. These additional soybean genes were: Glyma07g01730 encoding hypothetical protein with similarity to HAD superfamily, IIIB acid phosphatase, Glyma08g21410 encoding hypothetical protein with similarity to putative HAD superfamily, subfamily IIIB acid phosphatase, and Glyma10g39740, encoding thiazole biosynthetic enzyme (http://soykb.org/).

The control construct pDAB110167 for *N. benthamiana* transient expression contained an ScBV promoter fused to the Maize Streak Virus (MSV) 5' leader engineered to contain maize Alcohol dehydrogenaseI (AdhI) gene intron 6 paired with the terminator fragment from the potato Proteinase Inhibitor II (StPinII) (An, et al., Plant Cell. 1989 1:115-22) gene (abbreviated ScBV/StPinII) to drive expression of the RFP/AAD12 fusion reporter gene.

Example 2

Figure 3:
FIG. 3 A linear synthetic DNA fragment containing GmCAB promoter (SEQ ID NO:1), 5' UTR (SEQ ID NO:2), and terminator (SEQ ID NO:4) linked by the multiple cloning site and flanked by aatL1 and aatL2 recombination sites.

Cloning of the Candidate Soybean Regulatory Sequences for Expression in *N. benthamiana* Transient Assays The soybean genomic DNA SEQ ID NO:5 containing promoter sequence, 5' UTR and SEQ ID NO:4 containing terminator sequence of the Glyma08g08770 gene were synthesized by DNA2.0. A diagram of the synthetic fragment is shown in FIG. 3. The synthetic fragment was cloned in a Gateway entry vector, then the RFP/AAD12 reporter gene (SEQ ID NO:12) was inserted between the promoter/5'UTR and the terminator. The resulting expression cassette was moved to the final binary vector and used for transformation. The reporter gene was the dual reporter encoding a translational fusion protein containing the RFP and AAD12 polypeptides linked with the rigid helical peptide linker, LAE(EAAAK)$_5$AAA (SEQ ID NO: 28) described by Arai et al, (2001), Protein Eng, 14, 529-532; Marqusee et al, (1987), Proc Natl Acad Sci USA, 84, 8898-8902. The RFP/AAD12 reporter gene was engineered between the promoter/5'UTR and terminator and the resulting expression cassette incorporated in the binary vector pDAB116644 was used for plant transformation. This plant transformation vector also contained Green Fluorescent Protein (GFP) driven by the *Arabidopsis* Ubiquitin 10 promoter and 5' UTR *Agrobacterium* Orf23 terminator (AtuOrf23) and the synthetic pat gene (phosphinothricin N-acetyltransferase enzyme from *Streptomyces viridochromogenes*) driven by the Cassava vein mosaic virus (CsVMV) promoter (Samac et al, 2004, Transgenic Res, 13, 349-361) and *Agrobacterium* Orf1 terminator (AtuOrf1, Barker et al, 1983), Plant Mol Biol, 2, 335-350.)

Additional constructs that were used in experiments included pDAB116643 (Glyma07g01730, HAD superfamily, subfamily IIIB acid phosphatase), pDAB116645 (Glyma08g21410, HAD superfamily, subfamily IIIB acid phosphatase), and pDAB116646 (Glyma10g39740, thiazole biosynthetic enzyme).

The control construct used in *N. benthamiana* transient expression experiments pDAB110167 is described in EXAMPLE 1.

Example 3

*N. benthamiana* Leaf Infiltrations and Transient Assays of GmCAB Specified Expression of RFP/AAD12

*N. benthamiana* plants were grown in the greenhouse under 16-hour photoperiod, 27° C./24° C. Twenty four day old plants were used for infiltration. The 3-4 top-most leaves were infiltrated using two *Agrobacterium* strains. The first strain was used in all infiltrations and carried the pDAB112236 construct expressing P19 silencing suppressor (Silhavy et al, (2002), EMBO J, 21, 3070-3080; Voinnet et al, (1999), Proc Natl Acad Sci USA, 96, 14147-14152). The second *Agrobacterium* strain was either the experimental strain carrying pDAB116644 or a strain carrying the control binary vector pDAB110167. The pDAB110167 was identical to the pDAB116644 except that it had the reporter RFP/AAD12 fusion gene driven by ScBV/StPinII. For *N. benthamiana* leaf infiltrations *Agrobacterium* strains containing either pDAB116644 or pDAB110167 were mixed in equal proportions with an *Agrobacterium* strain that carried a plasmid that contained a gene encoding the P19 silencing suppressor. The mixing ratios were based on Optical Density (OD) readings. The density of all *Agrobacterium* cultures was adjusted to OD 2.0. After infiltration plants were maintained in a Conviron until leaves were collected on the 6$^{th}$ day after infiltration. Fluorescence data were collected using a Typhoon scanner from 30 leaves per construct with 3-5 one inch disks per leaf.

All samples from *N. benthamiana* were scanned on 3 channels: chlorophyll (488 nm blue laser, 670 nm BP30, 580 nm split), GFP (488 nm blue laser, 520 nm BP40, 580 nm split), and RFP (532 nm green laser, 580 nm BP30). The PMT setting were 340/340/400. Background adjustments were made by subtracting calculated means for non-treated and empty vector controls from test treatment values.

Results of testing in *N. benthamiana* transient assay are shown in Table 1. Analysis of results shows that Typhoon measured RFP fluorescence of pDAB116644 had ~5 fold higher mean RFP fluorescence relative to the control pDAB110167 construct. In contrast to results with GmCAB regulatory sequences (Table 1), additional constructs carrying candidate regulatory sequences from three other soybean endogenous genes pDAB116643 (Glyma07g01730), pDAB116645 (Glyma08g21410), pDAB116646 (Glyma10g39740) produced RFP fluorescence lower than that of the pDAB110167 control (Table 1). Failure of these constructs to produce significant RFP fluorescence was not due to poor infiltrations because present in the same constructs GFP transgene produced considerable levels of fluorescence (Table 1). Therefore, GmCAB expression cassette worked well for expressing transgenes, especially as compared to other endogenous soybean promoter candidates, which did not function well for transgene expression.

TABLE 1

Results of assaying RFP and GFP fluorescence in transiently transformed N. bethamiana leaves.

| Construct | n | RFP (pixels) | | | | GFP (pixels) | | | |
| --- | --- | --- | --- | --- | --- | --- | --- | --- | --- |
| | | Mean | Median | Std Dev | Std Err | Mean | Median | Std Dev | Std Err |
| pDAB110167 | 72 | 24746396.02 | 21007653.14 | 17820025.31 | 2100110.12 | 166966845.84 | 148985095.19 | 96809876.78 | 11409153.39 |
| pDAB116643 | 80 | 2066678.30 | 1274819.38 | 2546229.75 | 284677.14 | 203574692.56 | 183893252.80 | 100373867.56 | 11222139.55 |
| pDAB116644 | 80 | 116491051.27 | 107750622.86 | 60732885.00 | 6790142.97 | 98962191.22 | 82020272.98 | 50960661.98 | 5697575.22 |
| pDAB116645 | 80 | 14220964.68 | 9895119.64 | 14104613.24 | 1576943.70 | 229020644.27 | 222642186.51 | 95287405.32 | 10653455.78 |
| pDAB116646 | 80 | 8483450.53 | 7125700.79 | 5808075.30 | 649362.56 | 209859379.70 | 188156840.28 | 123171230.18 | 13770962.18 |

Example 4

Cloning of Candidate Soybean Regulatory Sequences for Expression in Soybean.

The soybean genomic DNA of SEQ ID NO:5 (containing promoter and 5' UTR) and SEQ ID NO:4 (containing terminator sequences) of the Glyma08g08770 gene were synthesized by DNA2.0. The synthetic fragment was cloned in a Gateway entry vector, and then the gene encoding the AAD12 protein was inserted between the 5'UTR and the terminator. The resulting expression cassette was moved to the final binary vector resulting in the final plasmid pDAB116629 that was used for transformation. The final plant transformation vector also contained the synthetic pat gene (phosphinothricin N-acetyltransferase enzyme from *Streptomyces viridochromogenes*) driven by CsVMV promoter and *Agrobacterium* Orfl terminator (AtuOrf1).

Example 5

Soybean Transformation

Ten to 20 transgenic $T_0$ *Glycine max* plants harboring expression vectors for nucleic acids comprising the promoter were generated as is known in the art, including for example by *Agrobacterium*-mediated transformation, as follows. Mature soybean (*Glycine max*) seeds were sterilized overnight with chlorine gas for sixteen hours. Following sterilization with chlorine gas, the seeds were placed in an open container in a LAMINAR™ flow hood to dispel the chlorine gas. Next, the sterilized seeds were imbibed with sterile $H_2O$ for sixteen hours in the dark using a black box at 24° C.

Preparation of split-seed soybeans. The split soybean seed comprising a portion of an embryonic axis protocol required preparation of soybean seed material that was cut longitudinally, using a #10 blade affixed to a scalpel, along the hilum of the seed to separate and remove the seed coat, and to split the seed into two cotyledon sections. Careful attention was made to partially remove the embryonic axis, wherein about ½-⅓ of the embryo axis remained attached to the nodal end of the cotyledon.

Inoculation. The split soybean seeds comprising a partial portion of the embryonic axis were then immersed for about 30 minutes in a solution of *Agrobacterium tumefaciens* (e.g., strain EHA 101 or EHA 105) containing binary plasmid comprising the promoter. The *Agrobacterium tumefaciens* solution was diluted to a final concentration of λ=0.6 $OD_{650}$ before immersing the cotyledons comprising the embryo axis.

Co-cultivation. Following inoculation, the split soybean seed was allowed to co-cultivate with the *Agrobacterium tumefaciens* strain for 5 days on co-cultivation medium (Wang, Kan. *Agrobacterium* Protocols. 2. 1. New Jersey: Humana Press, 2006. Print.) in a Petri dish covered with a piece of filter paper.

Shoot induction. After 5 days of co-cultivation, the split soybean seeds were washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds were then cultured on Shoot Induction I (SII) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed were transferred to the Shoot Induction II (SI II) medium containing SII medium supplemented with 6 mg/L glufosinate (LIBERTY®).

Shoot elongation. After 2 weeks of culture on SI II medium, the cotyledons were removed from the explants and a flush shoot pad containing the embryonic axis was excised by making a cut at the base of the cotyledon. The isolated shoot pad from the cotyledon was transferred to Shoot Elongation (SE) medium. The SE medium consisted of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures were transferred to fresh SE medium every 2 weeks. The cultures were grown in a CONVIRON™ growth chamber at 24° C. with an 18 h photoperiod at a light intensity of 80-90 µmol/m² sec.

Rooting. Elongated shoots which developed from the cotyledon shoot pad were isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots were transferred to rooting medium (MS salts, B5 vitamins, 28 mg/L Ferrous, 38 mg/L $Na_2EDTA$, 20 g/L sucrose and 0.59 g/L MES, 50 mg/L asparagine, 100 mg/L L-pyroglutamic acid, 7 g/L Noble agar, pH 5.6) in phyta trays.

Cultivation. Following culture in a CONVIRON™ growth chamber at 24° C., 18 h photoperiod, for 1-2 weeks, the shoots which developed roots were transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 µmol/m² sec under constant temperature (22° C.) and humidity (40-50%) for acclimatization of plantlets. The rooted plantlets were acclimated in sundae cups for several weeks before they were transferred to the greenhouse for further acclimatization and establishment of robust transgenic soybean plants.

TABLE 2

Primer and Probe Information for hydrolysis probe assay of pat and SpecR genes located in the backbone and internal reference (GMS116). All sequences are indicated 5'-3'.

| Oligo | Sequence | Type |
|---|---|---|
| PAT F | ACAAGAGTGGATTGATGATCTAGAGA (SEQ ID NO: 13) | Primer |
| PAT R | CTTTGATGCCTATGTGACACGTAAAC (SEQ ID NO: 14) | Primer |
| PAT PR | 6FAM-CCAGCGTAAGCAATACCAGCCACAACACC-3BHQ_1 (SEQ ID NO: 15) | Hydrolysis probe |
| SpecR F | CGCCGAAGTATCGACTCAACT (SEQ ID NO: 16) | Primer |
| SpecR R | GCAACGTCGGTTCGAGATG (SEQ ID NO: 17) | Primer |
| SpecR PR | 6FAM-TCAGAGGTAGTTGGCGTCATCGAG-3BHQ_1 (SEQ ID NO: 18) | Hydrolysis probe |

Development and morphological characteristics of transgenic lines were compared with non-transformed plants. Plant root, shoot, foliage and reproduction characteristics were compared. Plant shoot characteristics such as height, leaf numbers and sizes, time of flowering, floral size and appearance were recorded.

Example 6

Transgene Copy Number Estimation Using Real Time TaqMan® PCR

Leaf tissue samples from transgenic soybean plants and non-transgenic controls were collected in 96-well collection tubes. Tissue disruption was performed using tungsten 2 mm beads. Following tissue maceration, the genomic DNA was isolated in high throughput format using the MagAttract Plant kit (Qiagen, Hilden, Germany) on the Agilent BioCel. The transgenic copy number of pat was determined by using a hydrolysis probe assay, analogous to TaqMan® assay, in bi-plex with a soybean internal reference gene, GMS116. The assays were designed using the LightCycler® Probe Design Software 2.0. The transgenic presence/absence of Spectinomycin resistance gene (SpecR) was determined by using a hydrolysis probe assay, analogous to TaqMan® assay, in bi-plex with a soybean internal reference gene, GMS116. This assay was designed to detect the SpecR gene located within the backbone of the binary constructs used for transformation. Only events in which there was no amplification with SpecR probe were regenerated because this indicated that backbone fragments were not likely to be present in the transgenic soybean genome. For amplification of all genes of interest (pat, SpecR,GMS116), LightCycler® 480 Probes Master mix (Roche Applied Science, #04707494001) was prepared at 1× final concentration in a 10 µL volume multiplex reaction containing 0.4 µM of each primer and 0.2 µM of each probe (composition of primers and probes listed in Table 2). A two-step amplification reaction was performed using the LIGHTCYCLER 480 system (Roche Applied Science), with an extension at 60° C. for 60 seconds with fluorescence acquisition.

Analysis of real time PCR data was performed using LightCycler® software release 1.5 using the advanced relative quant module and was based on the ΔΔCt method. For pat, a sample of known single copy gDNA was included in each run and was used as a single copy calibrator. In addition, each run, for all genes of interest, included a wild-type (Maverick) sample as a negative control.

Example 7

Expression of Genes Operably Linked to Chlorophyll Binding Ab Regulatory Sequences in Soybean Protein Extraction from Soybean Leaves. The plants were sampled after they acclimated to growing in soil after transplantation from tissue culture vials. Two 6 mm diameter leaf discs were collected in a 96 well cluster tube rack and stored at −80° C. until the day of the analysis. Two DAISY™ steel 2 mm steel balls and 200 µl of extraction buffer (PBS solution containing 0.05% of Tween 20, 5 µl/ml of Sigma protease inhibitors, and 0.75% Ovabumin) was added to each tube. The samples were milled in a Kleco™ tissue pulverizer for 3 minutes, on maximum setting. Samples were centrifuged at 3,000×g for 5 minutes; 100 µl of the supernatant was transferred to an empty sample tube. Another 100 µl of extraction buffer was added to the plant sample and bead milled 3 additional minutes, centrifuged and 100 µl of this extract was combined with the first 100 µl. The combined supernatants were mixed and analyzed the same day as the extraction.

ELISA Quantitative Method for detection of AAD12 protein accumulation in soybean leaves. The AAD-12 pure proteins used in the experiment were expressed and purified in transgenic *Pseudomonas fluorescens* strains. Lyophilized transgenic and non-transgenic control tissue samples were used. Common biochemical and chemical reagents were purchased from Sigma-Aldrich Chemical Co. (St. Louis, Mo.). ELISA experiments were performed in 96-well microplates (Nunc, Roskilde, Denmark) and the absorbance was measured with a Vmax microplate reader (Molecular Devices, Menlo Park, Calif.) in dual-wavelength mode (450-650 nm). AAD-12 ELISA kit was purchased from Envirologix Inc (Portland, Me.).

Plant leaf samples (approximately 15 mg dry weight or 4 leaf punches) were analyzed for AAD-12. AAD-12 protein was extracted from plant tissues using the extraction buffer phosphate buffered saline with 0.05% Tween 20 (PBST) buffer with 0.75% albumin chicken egg (OVA) (PBST/OVA)(Sigma, St. Louis, Mo.). The extraction was performed in micofuge tubes with extraction buffer and two steel beads in a Geno-Grinder (BT&C/OPS Diagnostics, Bridgewater N.J.) for 1 minute at 1500 strokes/minute. The extract was centrifuged; the aqueous supernatant was collected, diluted, and assayed using an AAD-12 ELISA kit. An aliquot of the diluted sample was incubated with enzyme-conjugated anti-AAD-12 protein monoclonal antibody in the wells of an anti-AAD-12 polyclonal antibody coated plate in the sandwich ELISA format. At the end of the incubation period, the unbound reagents were removed from the plate by washing with PBST. The presence of AAD-12 was detected by incubating the antibody-bound enzyme conjugate with an enzyme substrate, generating a colored product. Since AAD-12 was bound in the antibody sandwich, the level of color development was proportional to the concentration of AAD-12 in the sample (i.e., lower protein concentrations result in lower color development). The color reaction was stopped by adding an acidic solution (0.4N $H_2SO_4$) and the absorbance at 450 nm minus absorbance at 650 nm was measured using a spectrophotometric plate reader. A calibration curve was estimated from the seven standard concentrations and their subsequent absorbance or optical density (OD) using a quadratic regression equation with a coefficient of determination of 0.990 or greater. The following formula was used for calculation:

$$y = A + Bx + Cx^2$$

Where y is the absorbance value (OD) and x is the antigen concentration.

Example 8

Whole Plant Soybean Stable Expression of Genes Operably Linked to Chlorophyll Binding Ab Regulatory Sequences.

To evaluate expression of the AAD12 gene fused to the GmCAB promoter, 5' UTR and terminator fragments, the stable transformation of the transgenes was detected in leaves of $T_0$ transgenic plants (See Examples 6 and 7). Transgenic events containing a low copy number of the transgene (1-2 copies) and showing no amplification with primers specific for the SpecR gene (Table 2) were regenerated and allowed to set seeds. The resulting $T_1$ seeds were germinated in the greenhouse and leaves were sampled for DNA extraction. DNA preparations were used for PCR amplification (Table 2 for primer sequences) to determine zygosity and reconfirm transgene copy number. Results confirmed that soybean plants carried transgene insertions and allowed separating plants in zygosity classes (homozygous, heterozygous and null). Homozygous and hemizygous plants were sampled for protein analysis by ELISA as described in EXAMPLE 7. Results of protein accumulation are shown in Table 3. All pDAB116629 transgenic events accumulated AAD12 protein in hemizygous and homozygous plants. This result demonstrated that GmCAB regulatory elements support accumulation of AAD12 protein in leaves of transgenic soybean plants. In contrast to GmCAB (pDAB116629), the other three candidate regulatory sequences (pDAB116628, pDAB116630, and pDAB116631) did not result in detectable accumulation of AAD12 protein (Table 3). This result clearly shows that GmCAB (SEQ ID NO:11) isolated from the Glyma08g08770 gene works well for driving transgene expression in soybean. At the same time, regulatory sequences from the other three genes Glyma07g01730 (pDAB116628), Glyma08g21410 (pDAB116630), and Glyma10g39740 (pDAB116631) do not result in detectable transgene expression in soybean and are not useable for transgene expression.

TABLE 3

Results of ELISA determination of AAD12 protein accumulation in leaves of $T_1$ transgenic soybean.

| Construct | Event | Zygosity AAD12 | Number of plants assayed | AAD12 ng/cm2 | | |
|---|---|---|---|---|---|---|
| | | | | Mean | Std Dev | Std Err |
| pDAB116628 | 116628[3]023 | Hemi | 4 | 0 | 0 | 0 |
| | | Homo | 3 | 0 | 0 | 0 |
| | 116628[3]041 | Hemi | 4 | 0 | 0 | 0 |
| | | homo | 4 | 0 | 0 | 0 |
| pDAB116629 | 116629[1]002 | hemi | 4 | 160.25 | 137.517 | 68.75848 |
| | | homo | 3 | 256.6667 | 5.773503 | 3.333333 |
| | 116629[1]046 | hemi | 4 | 157.5 | 68.98067 | 34.49034 |
| | | homo | 4 | 667.5 | 81.80261 | 40.9013 |
| | 116629[2]041 | hemi | 4 | 379.25 | 274.5583 | 137.2791 |
| | | homo | 4 | 363.5 | 350.9924 | 175.4962 |
| | 116629[2]087 | hemi | 4 | 160 | 45.46061 | 22.7303 |
| | | homo | 4 | 235 | 77.67453 | 38.83727 |
| pDAB116630 | 116630[1]001 | hemi | 4 | 0 | 0 | 0 |
| | | homo | 4 | 0 | 0 | 0 |
| pDAB116631 | 116631[2]025 | hemi | 4 | 0 | 0 | 0 |
| | | homo | 3 | 0 | 0 | 0 |
| | 116631[3]017 | hemi | 4 | 0 | 0 | 0 |
| | | homo | 4 | 0 | 0 | 0 |
| | 116631[3]021 | hemi | 4 | 0 | 0 | 0 |
| | | homo | 4 | 0 | 0 | 0 |
| | 116631[3]022 | hemi | 4 | 0 | 0 | 0 |
| | | homo | 4 | 0 | 0 | 0 |
| | 116631[4]089 | hemi | 4 | 0 | 0 | 0 |
| | | homo | 4 | 0 | 0 | 0 |
| Maverick | WT | Null | 12 | 0 | 0 | 0 |

Example 9

Herbicide Tolerance Specified by Expression of the Aad12 Gene Driven by the GmCAB Regulatory Sequences in Soybean $T_1$ Transgenic Plants.

To assess $T_1$ Soybean Herbicide Tolerance, $T_1$ seed generated from self-pollination of single copy $T_0$ events were planted in an artificial soil mix (MetroMix 360™) contained in 4-inch square pots. The $T_1$ generation is a segregating population of the homozygous, hemizygous and non-transgenic plants. To eliminate the null individuals, the $T_1$ population received a foliar application of 411 g active ingredient (ai)/ha glufosinate ammonium (Liberty® 280) when plants reached the first trifoliate leaf stage. Four days after application (DAA) surviving plants were sampled for molecular analysis to determine transgene zygosity and to confirm transgene copy number.

For each event, 8 homozygous and 8 hemizygous plants were sampled for protein analyses, and the following day (third trifoliate stage), half of the plants received a foliar application of 2240 g acid equivalent (ae)/ha 2,4-D dimethylamine (DMA) salt (Weedar® 64). The remaining plants received no spray application. Some plants were also sprayed with deionized water as a sprayer application control. In addition to the transformed events, the soybean variety, 'Maverick', was included in each treatment as a non-transformed control.

Foliar applications were made with a Mandel track sprayer set to deliver a spray solution at 187 L/ha to a spray area of 0.503 m² using an 8002E nozzle and a spray height of 18 inches above the plant canopy. Plant response to the 2,4-D application was evaluated at 5 hours after application (HAA) and 1, 7, and 14 DAA. Data were collected by assessment of visual injury and/or growth reduction as compared to untreated controls on a scale of 0% to 100% with 0% corresponding to no injury or growth reduction and 100% corresponding to complete plant death. Plants were maintained at 28° C./25° C. (day/night) under a 14 h photoperiod and sub-irrigated with water or fertilizer as needed.

Figure 4:
FIG. 4 is a photograph of representative soybean plants that illustrate the 2,4-D herbicide tolerance supported by expression of the aad12 gene driven by GmCAB regulatory sequences. Photo taken at 14 Days After Application (DAA).

Results of testing herbicide tolerance for soybean transgenic pDAB116629 plants and control plants are shown in Table 4. Assessment of the herbicide tolerance at 1 DAA of the herbicide revealed that transgenic plants carrying GmCAB regulatory sequences driven aad12 gene exhibited only mild phenotypic symptoms that are typical for this class of herbicides. These symptoms mostly included temporary leaf epinasty from which plants recovered within 24 hours. At the later time points (7 and 14 DAA), GmCAB transgenic plants exhibited no signs of damage from the herbicide spay, they grew normally and were not significantly different from the unsprayed control Maverick plants (FIG. 4). In contrast to the GmCAB transgenic plants (pDAB116629), the non-transgenic Maverick plants never recovered from treatment and died by 14 DAA (FIG. 4). These results show that GmCAB regulatory sequences support expression of the aad12 gene of interest at a level that is sufficient for commercial 2,4-D herbicide tolerance at high dosage spray of 2240 g ae/ha 2,4-D.

TABLE 4

Results of testing transgenic soybean plants herbicide tolerance that is specified by the GmCAB driven AAD12.

| | | | | Injury, % | | | | | | | | |
|---|---|---|---|---|---|---|---|---|---|---|---|---|
| | | | | 1 DAA | | | 7 DAA | | | 14 DAA | | |
| Construct | Event | Zygosity AAD12 | Number of plants examined | Mean | Std Dev | Std Err | Mean | Std Dev | Std Err | Mean | Std Dev | Std Err |
| pDAB116628 | 116628[3]023 | hemi | 4 | 28.8 | 2.5 | 1.3 | 21.3 | 2.5 | 1.3 | 2.5 | 13.8 | 1.3 |
| | | homo | 3 | 16.7 | 2.9 | 1.7 | 13.3 | 5.8 | 3.3 | 5.0 | 15.0 | 2.9 |
| | 116628[3]041 | hemi | 4 | 30.0 | 0.0 | 0.0 | 47.5 | 5.0 | 2.5 | 12.5 | 43.8 | 6.3 |
| | | homo | 4 | 30.0 | 0.0 | 0.0 | 28.8 | 2.5 | 1.3 | 2.5 | 23.8 | 1.3 |
| pDAB116629 | 116629[1]002 | hemi | 4 | 3.8 | 4.8 | 2.4 | 0.0 | 0.0 | 0.0 | 5.0 | 7.5 | 2.5 |
| | | homo | 3 | 3.3 | 5.8 | 3.3 | 5.0 | 8.7 | 5.0 | 5.8 | 3.3 | 3.3 |
| | 116629[1]046 | hemi | 4 | 10.0 | 0.0 | 0.0 | 0.0 | 0.0 | 0.0 | 2.5 | 1.3 | 1.3 |
| | | homo | 4 | 0.0 | 0.0 | 0.0 | 0.0 | 0.0 | 0.0 | 0.0 | 0.0 | 0.0 |
| | 116629[2]041 | hemi | 4 | 0.0 | 0.0 | 0.0 | 0.0 | 0.0 | 0.0 | 0.0 | 0.0 | 0.0 |
| | | homo | 4 | 0.0 | 0.0 | 0.0 | 0.0 | 0.0 | 0.0 | 0.0 | 0.0 | 0.0 |
| | 116629[2]087 | hemi | 4 | 0.0 | 0.0 | 0.0 | 0.0 | 0.0 | 0.0 | 0.0 | 0.0 | 0.0 |
| | | homo | 4 | 0.0 | 0.0 | 0.0 | 0.0 | 0.0 | 0.0 | 0.0 | 0.0 | 0.0 |
| pDAB116630 | 116630[1]001 | hemi | 4 | 37.5 | 5.0 | 2.5 | 26.3 | 2.5 | 1.3 | 0.0 | 15.0 | 0.0 |
| | | homo | 4 | 22.5 | 2.9 | 1.4 | 17.5 | 2.9 | 1.4 | 0.0 | 10.0 | 0.0 |
| pDAB116631 | 116631[2]025 | hemi | 4 | 35.0 | 4.1 | 2.0 | 47.5 | 5.0 | 2.5 | 14.1 | 40.0 | 7.1 |
| | | homo | 3 | 31.7 | 7.6 | 4.4 | 30.0 | 0.0 | 0.0 | 7.6 | 23.3 | 4.4 |
| | 116631[3]017 | hemi | 4 | 27.5 | 2.9 | 1.4 | 35.0 | 5.8 | 2.9 | 5.8 | 20.0 | 2.9 |
| | | homo | 4 | 30.0 | 9.1 | 4.6 | 26.3 | 2.5 | 1.3 | 6.3 | 18.8 | 3.1 |
| | 116631[3]021 | hemi | 4 | 30.0 | 0.0 | 0.0 | 45.0 | 5.8 | 2.9 | 8.5 | 38.8 | 4.3 |
| | | homo | 4 | 32.5 | 2.9 | 1.4 | 57.5 | 26.3 | 13.1 | 28.7 | 56.3 | 14.3 |
| | 116631[3]022 | hemi | 4 | 27.5 | 2.9 | 1.4 | 42.5 | 5.0 | 2.5 | 7.1 | 30.0 | 3.5 |
| | | homo | 4 | 31.3 | 6.3 | 3.1 | 31.3 | 6.3 | 3.1 | 4.8 | 23.8 | 2.4 |
| | 116631[4]089 | hemi | 4 | 35.0 | 4.1 | 2.0 | 55.0 | 10.0 | 5.0 | 20.0 | 40.0 | 10.0 |
| | | homo | 4 | 30.0 | 9.1 | 4.6 | 23.8 | 4.8 | 2.4 | 4.1 | 15.0 | 2.0 |
| Maverick | Maverick | null | 12 | 35.0 | 3.7 | 1.1 | 90.0 | 0.0 | 0.0 | 0.5 | 99.5 | 0.2 |

In contrast to the results with GmCAB regulatory sequences (Table 4), additional constructs carrying candidate regulatory sequences from three other soybean endogenous genes pDAB116628 (Glyma07g01730), pDAB116630 (Glyma08g21410), pDAB116631 (Glyma10g39740) suffered significant damage after treatment with 2,4-D herbicide (Table 4). Thus, these additional soybean candidate regulatory sequences were not acceptable for providing the desired tolerance to 2,4-D in this experiment. Accordingly, GmCAB worked surprisingly well for expressing transgenes, especially as compared to other endogenous soybean promoter candidates, which did not function well for transgene expression.

Example 10

Agrobacterium-Mediated Transformation of Arabidopsis and Molecular Analyses of Transgenic Events Arabidopsis thaliana ecotype Columbia was used for transformation. A standard Arabidopsis transformation procedure was used to produce transgenic seed by inflorescence dip method Clough et al, (1998), Plant J, 16, 735-743. The $T_1$ seeds were sown on selection trays (10.5"×21"×1", T.O. Plastics Inc., Clearwater, Minn.). For this, 200 mg of cold stratified seeds (0.1% agar+385 mg/L Liberty for 48 hours before sowing) were distributed on selection trays using a modified air driven spray apparatus to distribute 10 ml of seed suspension per selection tray. Trays were covered with humidity domes, marked with seed identifier, and placed in a Conviron with an individual watering tray under each flat. The humidifying dome was removed approximately 5 days post-sowing. The first watering of selection trays used sub-irrigation with Hoagland's fertilizer at approximately 10-14 days post-sowing. In addition to stratification with the herbicide, plants were sprayed with a 0.2% solution (20 µl/10 mL distilled $H_2O$) of Liberty 7 and 9 days post-sowing. $T_1$ plants tolerant to Liberty were transplanted from selection trays into 2-inch pots and allowed to grow for 7-10 days before sampling for molecular analysis. Based on the results of molecular analysis a subset of plants with single transgene copies were retained for further analyses.

DNA was extracted from leaves using an approximately 0.5 square centimeter of Arabidopsis leaf that was pinched off each plant. Samples were collected in a 96-well DNA extraction plate (Qiagen™, #19560). 200 ul of extraction buffer was added to each well and tissue was disrupted with 3 mm stainless steel beads using a Kleco™ tissue pulverizer (3 minutes on the maximum setting). After tissue maceration, DNA was isolated using the BioSprint 96 DNA Plant Kit™ (Qiagen, #941558).

For qPCR, transgene copy number was assayed using hydrolysis probe designed to detect the pat and aad12 genes (Table 5). The Arabidopsis endogenous gene, AtTaftl15, was used for normalization of DNA template concentration (Table 5). qPCR was performed as follows: 10 µl of Probes Master Mix (Roche Applied Science, #04707494001) with final concentration of 0.4 µM of each primer and 0.2 µM of each probe. PCR cycles were performed using 95° C. for 10 min, followed by 40 amplification cycles (95° C. for 1 min, 60° C. for 40 sec, and 72° C. for 1 sec) and 40° C. for 1 sec. All qPCR assays were run in bi-plex format, with pat or aad12 assays paired with assay for the endogenous gene AtTaftI-15. Cp scores, the point at which the florescence signal crosses the background threshold using the advanced relative quantification algorithm, based on the ΔΔCt method, (LightCycler® software release 1.5) was used to perform the analysis of real time PCR data. All samples were calibrated to a known hemizygous plant to obtain the transgene copy number.

TABLE 5

Primers and probes used for genotyping and zygosity analyses of Arabidopsis transgenic plants

| Oligo name | Oligo Sequence | Fluorophore label | Target gene |
| --- | --- | --- | --- |
| AtTafII F | GAGGATTAGGGTTTCAACGGAG (SEQ ID NO: 19) | | AtTafII-15 |
| AtTafII R | GAGAATTGAGCTGAGACGAGG (SEQ ID NO: 20) | | AtTafII-15 |
| AtTafIII Probe | AGAGAAGTTTCGACGGATTTCGGGC (SEQ ID NO: 21) | HEX | AtTafII-15 |
| PAT A primer | ACAAGAGTGGATTGATGATCTAGAGAGGT (SEQ ID NO: 22) | | PAT |
| PAT S primer | CTTTGATGCCTATGTGACACGTAAACAGT (SEQ ID NO: 23) | | PAT |
| PAT_AS probe | AGGGTGTTGTGGCTGGTATTGCTTACGCT (SEQ ID NO: 24) | Cy5 | PAT |
| AAD12 F | CAGAGTCCATGCTCACCAAT (SEQ ID NO: 25) | | AAD12 |
| AAD12 R | ACGTGGCAACTTGAAATCC (SEQ ID NO: 26) | | AAD12 |
| AAD12 Probe | TGGAGATGTGGTTGTGTGGGACAA (SEQ ID NO: 27) | Cy5 (T1) or FAM (T2) | AAD12 |

Up to 100 Liberty tolerant single copy T₁ events were screened by qPCR to identify single copy transgene events (Table 6). Single copy transgenic events shown in Table 6 were used for further analyses of transgene expression in T₁ transgenic plants.

TABLE 6

Results of copy number analyses for *Arabidopsis* T₁ transgenes

| Construct | Estimated transgene copy number | | | |
|---|---|---|---|---|
| | Single copy events | Fragmented events | Multiple Copy events | Total events analyzed |
| pDAB116643 | 10 | 6 | 84 | 100 |
| pDAB116644 | 12 | 13 | 74 | 99 |
| pDAB116645 | 11 | 8 | 79 | 98 |
| pDAB116646 | 9 | 17 | 66 | 92 |
| Total | 48 | 65 | 372 | 485 | fluorescence relative to the background fluoresce detected in wild type control (Wt). In contrast, the other three candidate regulatory sequences from soybean (contained in pDAB116643, pDAB116645 and pDAB115546 constructs) produced low, similar to the Wt control RFP fluorescence. Low RFP fluorescence from pDAB116643, pDAB116645 and pDAB115546 was in contrast to comparable fluorescence from the GFP transgene which was significantly higher than background in all tested constructs. This result clearly shows that GmCAB (SEQ ID NO:11) isolated from the Glyma08g08770 gene works well for driving transgene expression in transgenic *Arabidopsis*. At the same time, regulatory sequences from the other three genes (Glyma07g01730, Glyma08g21410 and Glyma10g39740) do not result in acceptable levels of transgene expression.

TABLE 7

Results of testing expression of RFP/AAD12 reporter expression in transgenic T₁ *Arabidopsis* plants

| Plasmid | # of plants | RFP (pixels/cm2) | | | | GFP (pixels/cm2) | | | |
|---|---|---|---|---|---|---|---|---|---|
| | | Mean | Median | Std Dev | Std Err | Mean | Median | Std Dev | Std Err |
| pDAB116643 | 10 | 805.53 | 699.82 | 317.53 | 100.41 | 3800.59 | 3806.43 | 1203.14 | 380.47 |
| pDAB116644 | 12 | 5581.77 | 5376.69 | 1366.34 | 394.43 | 4293.02 | 4378.08 | 743.06 | 214.50 |
| pDAB116645 | 11 | 1196.73 | 939.33 | 584.75 | 176.31 | 3358.36 | 3397.92 | 703.70 | 212.17 |
| pDAB116646 | 9 | 758.97 | 765.84 | 172.95 | 57.65 | 2337.78 | 2309.31 | 338.94 | 112.98 |
| Wt | 5 | 884.07 | 777.24 | 256.06 | 114.51 | 563.88 | 510.18 | 107.63 | 48.14 |

Example 11

Evaluation of Genes Operably Linked to Chlorophyll Binding Ab Regulatory Sequences in T *Arabidopsis* Plants To evaluate expression of the RFP/AAD12 reporter driven by the GmCAB promoter, 5' UTR and terminator fragments, single copy transgenic events were identified and assayed for RFP fluorescence using Typhoon instrument.

All samples from *Arabidopsis* were scanned on 3 channels: chlorophyll (488 nm blue laser, 670 nm BP30, 580 nm split), GFP (488 nm blue laser, 520 nm BP40, 580 nm split), and RFP (532 nm green laser, 580 nm BP30). The PMT setting were 500/500/500 for leaves. Background adjustments were made by subtracting calculated means for non-treated and empty vector controls from test treatment values. The values from each leaf were averaged to generate a mean fluorescence value.

For analyses of fluorescence in rosette leaves, fully expanded leaves from single copy transgenic events were harvested from each plant and scanned from adaxial (top) side. The "Contour draw" function was used to outline leaf shapes and normalized fluorescence was determined by dividing signal volume by surface of the leaf.

Results of testing in T₁ *Arabidopsis* plants are shown in Table 7. Analysis of RFP fluorescence revealed that GmCAB (pDAB116644) supported high levels of RFP Example 12

Expression of Genes Operably Linked to Chlorophyll Binding Ab Regulatory Sequences in T₂ *Arabidopsis* Transgenic Plants The pDAB116644 construct exhibited high RFP/AAD12 fluorescence in TiArabidopsis (EXAMPLE 11). Therefore, this construct was advanced for characterization in T₂ *Arabidopsis* plants. The constructs with low to no detectable expression (pDAB116643, pDAB116645, pDAB11646) were not tested in T₂. Seven high to medium RFP/AAD12 expressing transgenic events of pDAB116644 were selected for T₂ testing and 56 plants were grown for each of the events. T₂ plants were molecularly genotyped as described in EXAMPLE 10. Based on molecular analysis, all homozygous and a comparable number of hemizygous plants were retained for transgene expression analysis and herbicide tolerance tests (see EXAMPLE 13).

Fully expanded *Arabidopsis* rosette leaves were collected and scanned for RFP fluorescence as described in EXAMPLE 10 and results are shown in Table 8. Results revealed that hemizygous (Hemi) and homozygous (Homo) transgenic plants from all seven transgenic events exhibited high RFP fluorescence relative to the non-transgenic siblings (shown as "Null" in Table 8). As expected, increased transgene copy number in the homozygous plants (two transgene copies) resulted in a higher mean RFP fluorescence levels relative to the mean hemizygous plants (one transgene copy). These results clearly illustrate that GmCAB in pDAB116644 supports heritable, copy number-dependent, transgene expression.

TABLE 8

Results of testing pDAB116644 expression of RFP fluorescence specified by expression of RFP/AAD12 reporter in transgenic T₂ Arabidopsis plants

| | | | RFP | | | | GFP | | | |
|---|---|---|---|---|---|---|---|---|---|---|
| Event | Zygosity | # of plants | Mean | Median | Std Dev | Std Err | Mean | Median | Std Dev | Std Err |
| 116644[2]-008 | Hemi | 5 | 4227.83 | 3365.32 | 1349.80 | 603.65 | 5980.03 | 5669.61 | 827.84 | 370.22 |
| | Homo | 12 | 9877.51 | 9129.40 | 2593.92 | 748.80 | 13472.82 | 13373.16 | 899.74 | 259.73 |
| | Null | 3 | 362.80 | 346.26 | 42.73 | 24.67 | 814.04 | 809.18 | 16.24 | 9.38 |
| 116644[2]-015 | Hemi | 5 | 6016.97 | 6026.49 | 932.58 | 417.06 | 6272.94 | 6438.40 | 320.72 | 143.43 |
| | Homo | 13 | 11843.60 | 12301.15 | 1757.28 | 487.38 | 11599.19 | 11922.96 | 1355.02 | 375.82 |
| | Null | 3 | 331.36 | 309.34 | 65.42 | 37.77 | 731.37 | 732.46 | 24.05 | 13.89 |
| 116644[2]-028 | Hemi | 5 | 4573.01 | 3616.05 | 2593.47 | 1159.83 | 8869.02 | 5457.23 | 8461.46 | 3784.08 |
| | Homo | 11 | 6514.90 | 6686.95 | 3229.19 | 1021.16 | 10103.96 | 9966.78 | 5677.07 | 1795.25 |
| | Null | 3 | 338.75 | 332.62 | 155.53 | 89.79 | 631.49 | 735.85 | 241.11 | 139.20 |
| 116644[2]-044 | Hemi | 5 | 4011.18 | 4550.02 | 1483.35 | 663.37 | 4186.11 | 4622.94 | 1487.13 | 665.07 |
| | Homo | 12 | 9835.07 | 8734.54 | 5340.33 | 1610.17 | 11433.59 | 10702.57 | 6104.29 | 1840.51 |
| | Null | 3 | 338.30 | 364.99 | 107.87 | 62.28 | 900.78 | 1041.54 | 261.96 | 151.24 |
| 116644[2]-048 | Hemi | 5 | 2959.23 | 2710.29 | 998.95 | 446.75 | 4609.36 | 4241.30 | 1395.82 | 624.23 |
| | Homo | 11 | 5598.51 | 5465.46 | 1464.14 | 441.45 | 9606.32 | 9732.45 | 2861.09 | 862.65 |
| | Null | 3 | 246.80 | 247.76 | 25.94 | 14.97 | 532.51 | 493.67 | 67.34 | 38.88 |
| 116644[2]-068 | Hemi | 5 | 3150.10 | 2365.64 | 2179.38 | 974.65 | 4852.67 | 3695.63 | 3498.09 | 1564.39 |
| | Homo | 8 | 5477.65 | 5199.28 | 1381.71 | 488.51 | 9539.53 | 10092.40 | 3877.65 | 1370.96 |
| | Null | 3 | 111.16 | 117.41 | 26.99 | 15.58 | 272.18 | 280.05 | 78.96 | 45.59 |
| 116644[2]-071 | Hemi | 4 | 2387.64 | 2406.58 | 446.20 | 223.10 | 1853.91 | 1826.86 | 474.70 | 237.35 |
| | Homo | 12 | 6223.22 | 5933.59 | 1715.25 | 495.15 | 5519.19 | 5150.17 | 1667.46 | 481.35 |
| | Null | 3 | 226.54 | 258.13 | 76.28 | 44.04 | 491.14 | 573.78 | 174.97 | 101.02 |
| Wt | Null | 3 | 130.89 | 132.81 | 19.75 | 11.40 | 290.25 | 294.69 | 16.16 | 9.33 |

Example 13

Herbicide Tolerance Specified by Expression of the RFP/AAD12 Reporter Driven by the GmCAB Regulatory Sequences in Arabidopsis T₂ Plants Sprayed with 2,4-D Herbicide at the Rosette and Bolting Stages To test 2,4-D tolerance, Arabidopsis T₂ plants were sprayed with four concentrations of 2,4-D dimethylamine salt (DMA) (280, 560, 1120, 2240 g ae/ha). The commercial formulation of Weedar 64 (456 g ae/L 2,4-dimethylamine, Bayer CropScience) was used for the spray application. These concentrations correspond to 1×, 2×, 3× and 4× levels of 2,4-D applications required to control non-transformed Arabidopsis, respectively. Spraying was completed at rosette and bolting stages using a stationary Mandel track sprayer (Mandel Scientific Company Ltd.). The Mandel track sprayer was calibrated to deliver 187 L/ha with a fan tip nozzle (TeeJet, 8002E).

The RFP/AAD12 fusion reporter gene allows characterization of both the transgene expression through fluorescence of RFP, as well as herbicide tolerance to 2,4-D via the presence of the functional AAD12 peptide within the RFP/AAD12 fusion reporter. pDAB116644 plants were sprayed with 2,4-D herbicide at the rosette and bolting stages of development. Genotyped non-transgenic "null" plants were used as controls for damage caused by 2,4-D applications. As a positive control for this experiment, we used the pDAB4468 transgenic plants that carried AAD12 driven by the Arabidopsis Ubiquitin10 (AtUbi 10) promoter and Agrobacterium Orf23 terminator (AtuOrf23) described in Wright et al, (2010), Proc Natl Acad Sci USA, 107, 20240-20245. Visual assessment of plant damage was conducted at 14 days after application (DAA) and recorded using a visual percent damage grading scale of 0% through 100%; where 0% damage is equivalent to the untreated control and 100% damage is complete damage.

Figure 5:
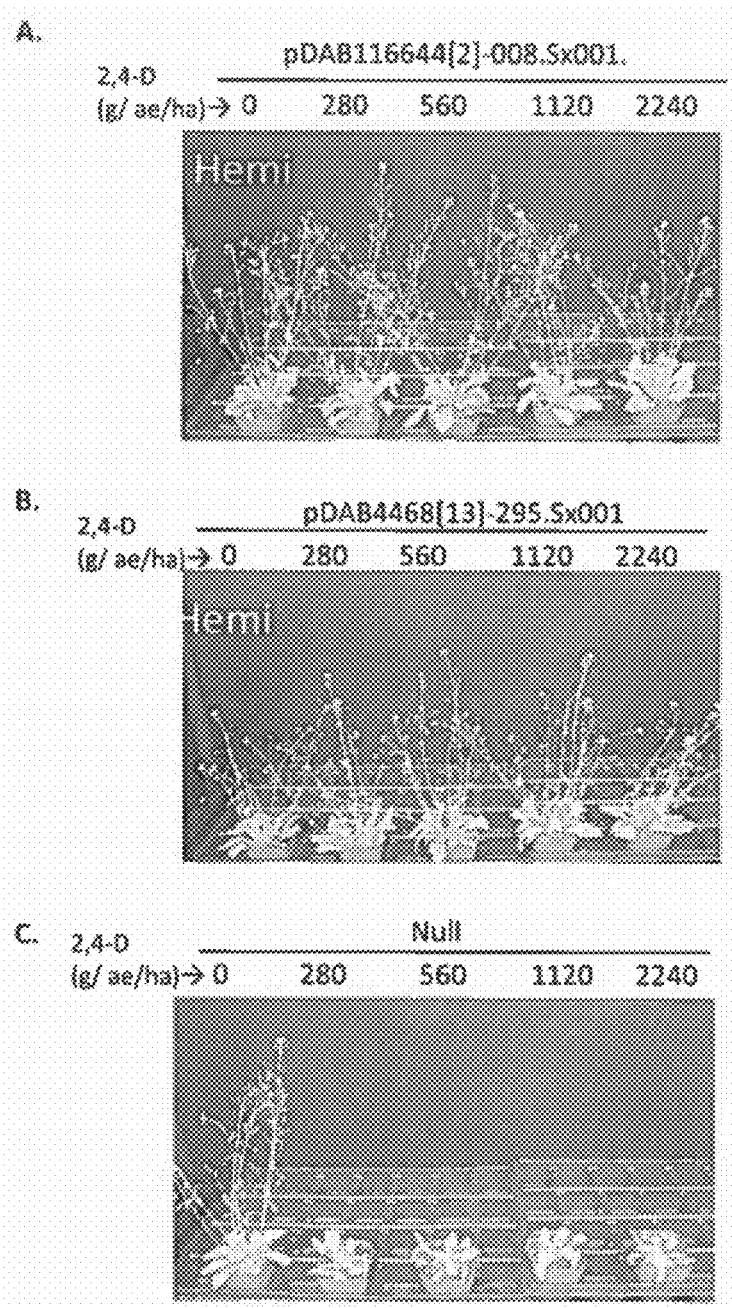
FIG. 5 is the compilation of photos of *Arabidopsis* plants sprayed at the rosette stage with 2,4-D. Photos of representative plants were taken on 7 DAA. Event ID and 2,4-D spray doses are indicated above each photo. A. Representative plants from the pDAB116644 construct after the spray with various doses of 2,4-D. B. Representative plants from the pDAB4468 control construct after the spray with the various doses of 2,4-D. C. Representative non-transgenic (Null) plants after spraying with variable doses of 2,4-D herbicide.

Data analyses of 2,4-D tolerance at the rosette stage (Table 9, FIG. 5A) demonstrated that all seven tested transgenic events of pDAB116644 were tolerant to both, lower (280 and 560 g ae/ha) and higher (1120 and 2240 g ae/ha), 2,4-D application rates. This result shows that GmCAB (SEQ ID NO: 11) drives expression of the RFP/AAD12 fusion at the levels that are sufficient for the robust 2,4-D tolerance. As expected 100% damage was observed for non-transgenic (Null) controls (Table 9, FIG. 5C). The tolerance of pDAB116644 events was similar to the four out of five events of the positive pDAB4468 control, (Table 9, FIG. 5B). Surprisingly, one out of five pDAB4468 events (4468[13]-279) was susceptible to 2,4-D (Table 9), suggesting the possibility of spontaneous transgene silencing in this event. Therefore, in respect of 2,4-D tolerance, the seven transgenic events of pDAB116644 performed similar or better than the five events for the control pDAB4468 construct.

TABLE 9

Summary of 2,4-D injury (%) at 14 DAA for T₂ Arabidopsis sprayed at rosette stage

| Transgenic event | Transgene zygosity[1] | Number of plants tested | Application Rate (g ae/ha 2,4-D) | % Injury Mean | Std dev |
|---|---|---|---|---|---|
| 116644[2]-008 | All hemi | 3 | 0 | 0 | 0 |
| | All hemi | 3 | 280 | 0 | 0 |
| | All hemi | 3 | 560 | 0 | 0 |
| | All hemi | 3 | 1120 | 2 | 0 |
| | All hemi | 3 | 2240 | 8 | 0 |
| 116644[2]-015 | All hemi | 4 | 0 | 0 | 0 |
| | All hemi | 4 | 280 | 0 | 0 |
| | All hemi | 4 | 560 | 0 | 0 |
| | All hemi | 4 | 1120 | 1.5 | 1 |
| | All hemi | 3 | 2240 | 11.5 | 9.1 |

TABLE 9-continued

Summary of 2,4-D injury (%) at 14 DAA for T₂ *Arabidopsis* sprayed at rosette stage

| Transgenic event | Transgene zygosity[1] | Number of plants tested | Application Rate (g ae/ha 2,4-D) | % Injury Mean | Std dev |
|---|---|---|---|---|---|
| 116644[2]-028 | All hemi | 4 | 0 | 0 | 0 |
| | All hemi | 4 | 280 | 0 | 0 |
| | All hemi | 4 | 560 | 0 | 0 |
| | All hemi | 4 | 1120 | 3.8 | 2.5 |
| | All hemi | 3 | 2240 | 31.8 | 42.2 |
| 116644[2]-044 | All hemi | 4 | 0 | 0 | 0 |
| | All hemi | 4 | 280 | 0 | 0 |
| | All hemi | 4 | 560 | 0 | 0 |
| | All hemi | 4 | 1120 | 4.5 | 3.3 |
| | All hemi | 2 | 2240 | 28.3 | 31.6 |
| 116644[2]-048 | Hemi 3, Homo 1 | 4 | 0 | 0 | 0 |
| | Hemi 4 | 4 | 280 | 12 | 19 |
| | Hemi 3, homo 1 | 4 | 560 | 0 | 0 |
| | Hemi 2, Homo 2 | 4 | 1120 | 3.8 | 7.5 |
| | Hemi 2, Homo 2 | 4 | 2240 | 9 | 4.2 |
| 116644[2]-068 | All hemi | 4 | 0 | 0 | 0 |
| | All hemi | 4 | 280 | 0 | 0 |
| | All hemi | 4 | 560 | 0 | 0 |
| | All hemi | 3 | 1120 | 23.8 | 47.5 |
| | All hemi | 4 | 2240 | 12.8 | 1.5 |
| 116644[2]-071 | All hemi | 4 | 0 | 0 | 0 |
| | All hemi | 4 | 280 | 0 | 0 |
| | All hemi | 4 | 560 | 0 | 0 |
| | All hemi | 4 | 1120 | 0 | 0 |
| | All hemi | 4 | 2240 | 10 | 0 |
| 4468[13]-279 | Hemi 3, homo 1 | 4 | 0 | 0 | 0 |
| | Hemi 3, homo 1 | 4 | 280 | 99 | 0 |
| | Hemi 2, homo 2 | 4 | 560 | 99 | 0 |
| | Hemi 2, homo 3 | 5 | 1120 | 94 | 11 |
| | Hemi 2, homo 2 | 4 | 2240 | 99 | 0 |
| 4468[13]-295 | Hemi 2, homo 2 | 4 | 0 | 0 | 0 |
| | Hemi 3, homo 1 | 4 | 280 | 0 | 0 |
| | Hemi 2, homo 2 | 4 | 560 | 0 | 0 |
| | Hemi 2, homo 1 | 3 | 1120 | 0 | 0 |
| | Hemi 2, homo4 | 4 | 2240 | 0 | 0 |
| 4468[13]-297 | Hemi 2, homo 2 | 4 | 0 | 0 | 0 |
| | Hemi 2, homo 2 | 4 | 280 | 0 | 0 |
| | Hemi 2, homo 2 | 4 | 560 | 0 | 0 |
| | Hemi 2, homo 2 | 4 | 1120 | 2 | 0 |
| | Hemi 2, homo 2 | 4 | 2240 | 2.8 | 1.5 |
| 4468[13]-314 | Hemi 2, homo 2 | 4 | 0 | 0 | 0 |
| | Hemi 2, homo 2 | 4 | 280 | 0 | 0 |
| | Hemi 2, homo 2 | 4 | 560 | 0 | 0 |
| | Hemi 2, homo 2 | 4 | 1120 | 0 | 0 |
| | Hemi 2, homo 2 | 4 | 2240 | 8 | 0 |
| 4468[13]-335 | Hemi 2, homo 2 | 4 | 0 | 0 | 0 |
| | Hemi 3, homo 1 | 4 | 280 | 0 | 0 |
| | Hemi 2, homo 2 | 4 | 560 | 0 | 0 |
| | Hemi 2, homo 2 | 4 | 1120 | 0.5 | 1 |
| | Hemi 2, homo 2 | 4 | 2240 | 8 | 0 |
| 116644[2]-008 | All null | 4 | 0 | 5 | 0 |
| | All null | 4 | 280 | 97.5 | 2.9 |
| | All null | 4 | 560 | 95 | 0 |
| | All null | 4 | 1120 | 99.3 | 0.5 |
| | All null | 4 | 2240 | 100 | 0 |
| 116644[2]-048 | All null | 0 | 0 | 0 | 0 |
| | All null | 2 | 280 | 90 | 0 |
| | All null | 2 | 560 | 95 | 0 |
| | All null | 2 | 1120 | 100 | 0 |
| | All null | 2 | 2240 | 100 | 0 |
| 116644[2]-028 | All null | 3 | 0 | 0 | 0 |
| | All null | 3 | 280 | 90 | 0 |
| | All null | 3 | 560 | 95 | 0 |
| | All null | 3 | 1120 | 100 | 0 |
| | All null | 3 | 2240 | 100 | 0 |
| 4468[13]-314 | All null | 3 | 0 | 0 | 0 |
| | All null | 3 | 280 | 90 | 0 |
| | All null | 3 | 560 | 95 | 0 |
| | All null | 3 | 1120 | 100 | 0 |
| | All null | 3 | 2240 | 100 | 0 |

[1]Plants with homo and hemi zygosity were pooled for this test for some of the events, thus the results are not separated by zygosity in this cases.

Figure 6:
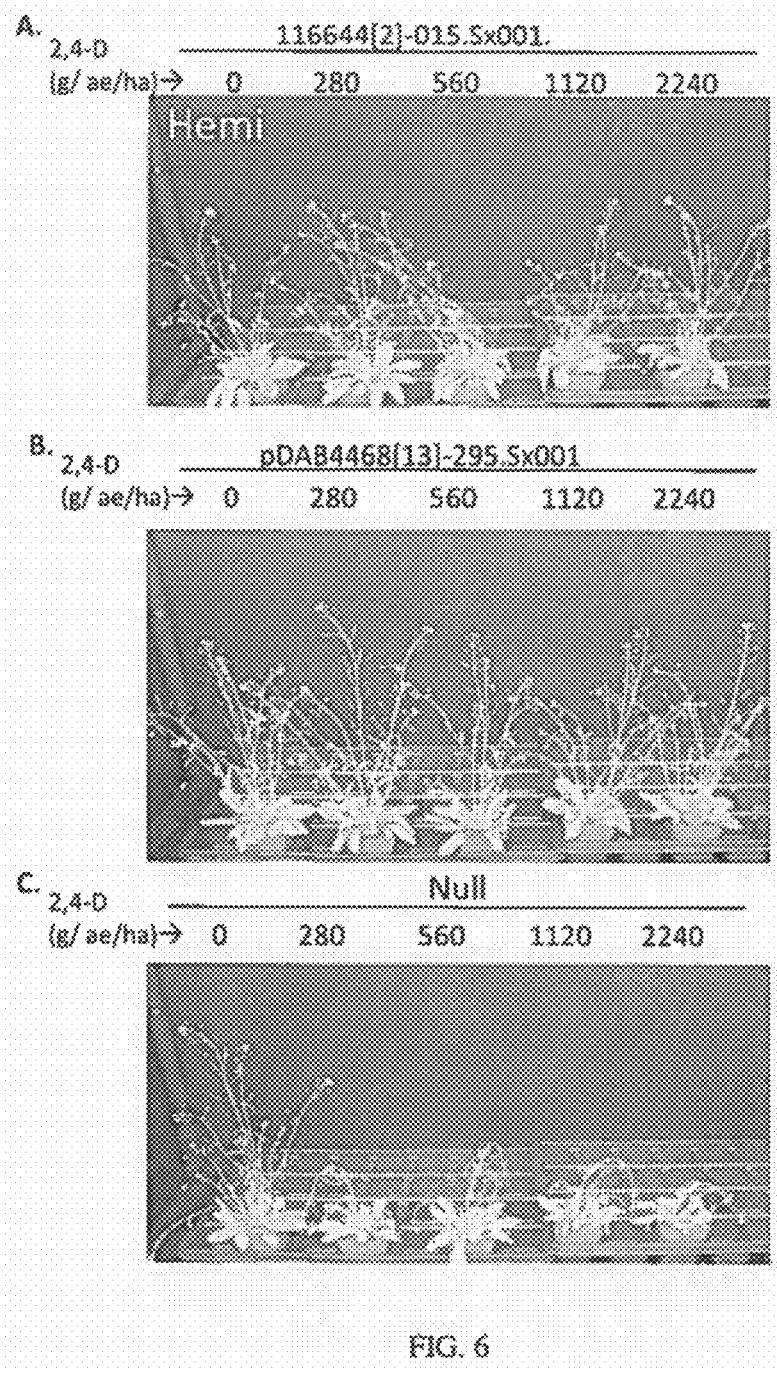
FIG. 6 is the compilation of photos of *Arabidopsis* plants sprayed at the bolting stage with 2, 4-D. Photos of representative plants were taken on 7 DAA. Event ID and 2,4-D spray doses are indicated above each photo. A. Representative plants from the pDAB116644 construct after the spray with the various doses of 2,4-D. B. Representative plants from the pDAB4468 construct after the spray with the various doses of 2, 4-D. C. Representative non-transgenic (Null) plants after spraying with variable doses of 2,4-D herbicide.

Similar to the results at the rosette stage, analysis of the pDAB116644 plants at the bolting stage revealed robust 2,4-D tolerance when RFP/AAD12 expression was controlled by GmCAB in pDAB116644 (Table 10, FIG. 6A). For this construct, no abortion of flowers or siliques was observed after spraying at high (2240 g ae/ha) 2,4-D dose (not shown), indicating that there was no impact on reproductive tissues development. Analyses of the control pDAB4468 construct exhibited robust tolerance for one of the used events (4468[13]-295, Table 10, FIG. 6B), while reduced tolerance was observed for the second pDAB4468 event (4468[13]-279, Table 10). Reduced 2,4-D tolerance for the latter pDAB4468 event is consistent with poor performance of this event at rosette stage, therefore suggesting the loss of transgene expression, and consequently poor 2,4-D tolerance in this event (Table 9). As expected, non-transgenic (Null) plants were highly susceptible to 2,4-D application at bolting stage (Table 10, FIG. 6C). These results, therefore, demonstrate that GmCAB (SEQ ID NO:11) in pDAB116644 drives robust 2,4-D tolerance that is equal or better than that by the control pDAB4468 construct, even when plants are sprayed at the later developmental stages.

TABLE 10

Summary of 2,4-D injury (%) at 14 DAA for T₂ *Arabidopsis* sprayed at the bolting stage

| Transgenic events included in the test | Transgene zygosity | Number of plants tested | Application Rate (g ae/ha 2,4-D) | % Injury Analysis Mean | Std dev |
|---|---|---|---|---|---|
| 116644[1] | All hemi | 3 | 0 | 0 | 0 |
| | All hemi | 1 | 280 | 0 | — |
| | All hemi | 3 | 560 | 2 | 3 |
| | All hemi | 1 | 1120 | 2 | — |
| | All hemi | 3 | 2240 | 22 | 24 |
| 4468[13]-279 | All hemi | 2 | 0 | 0 | 0 |
| | All hemi | 2 | 280 | 30 | 0 |
| | All hemi | 2 | 560 | 35 | 49 |
| | All hemi | 2 | 1120 | 70 | 0 |
| | All hemi | 2 | 2240 | 85 | 0 |
| 4468[13]-295 | All hemi | 2 | 0 | 0 | 0 |
| | All hemi | 2 | 280 | 0 | 0 |
| | All hemi | 2 | 560 | 40 | 42 |
| | All hemi | 2 | 2240 | 5 | 0 |
| 116644[2] | All null | 2 | 0 | 0 | 0 |
| | All null | 2 | 280 | 80 | 0 |
| | All null | 2 | 560 | 80 | 0 |
| | All null | 2 | 1120 | 90 | 0 |
| | All null | 2 | 2240 | 95 | 0 |

TABLE 10-continued

Summary of 2,4-D injury (%) at 14 DAA for
T$_2$ Arabidopsis sprayed at the bolting stage

| Transgenic events included in the test | Transgene zygosity | Number of plants tested | Application Rate (g ae/ ha 2,4-D) | % Injury Analysis Mean | Std dev |
|---|---|---|---|---|---|
| 4468[3] | All null | 2 | 0 | 0 | 0 |
| | All null | 2 | 280 | 70 | 0 |
| | All null | 2 | 560 | 75 | 7 |
| | All null | 42 | 1120 | 90 | 0 |
| | All null | 2 | 2240 | 95 | 0 |

[1]For this construct, transgenic plants from events 116644[2]-015.Sx001, 116644[2]-048.Sx001, 116644[2]-068.Sx001, 116644[2]-071.Sx001 were pooled for the 2,4-D spray application.
[2]For this construct, Null plants from events 116644[2]-015, 116644[2]-068, and 116644[2]-071 were pooled for the 2,4-D spray application.
[3]For this construct, Null plants from events 4468[13]-279 and 4468[13]-295 were pooled for the 2,4-D spray application.

Example 14

Cotton Transformation

Cotton is transformed with the promoter (with or without a chloroplast transit peptide) to drive gene expression by utilizing a method known to those of skill in the art, for example, substantially the same techniques previously described in EXAMPLE 14 of U.S. Pat. No. 7,838,733, or Example 12 of PCT International Patent Publication No. WO 2007/053482, herein incorporated by reference.

Example 15

*Agrobacterium*-Mediated Transformation of Canola (*Brassica napus*) Hypocotyls

*Agrobacterium* Preparation. The *Agrobacterium* strain containing the binary plasmid is streaked out on YEP media (Bacto Peptone™ 20.0 gm/L and Yeast Extract 10.0 gm/L) plates containing streptomycin (100 mg/ml) and spectinomycin (50 mg/mL) and incubated for 2 days at 28° C. The propagated *Agrobacterium* strain containing the binary plasmid is scraped from the 2-day streak plate using a sterile inoculation loop. The scraped *Agrobacterium* strain containing the binary plasmid is then inoculated into 150 mL modified YEP liquid with streptomycin (100 mg/ml) and spectinomycin (50 mg/ml) into sterile 500 mL baffled flask(s) and shaken at 200 rpm at 28° C. The cultures are centrifuged and resuspended in M-medium (LS salts, 3% glucose, modified B5 vitamins, 1 µM kinetin, 1 µM 2,4-D, pH 5.8) and diluted to the appropriate density (50 Klett Units as measured using a spectrophotometer) prior to transformation of canola hypocotyls.

Canola Transformation

Seed germination: Canola seeds (var. NEXERA710™) are surface-sterilized in 10% Clorox™ for 10 minutes and rinsed three times with sterile distilled water (seeds are contained in steel strainers during this process). Seeds are planted for germination on ½ MS Canola medium (½ MS, 2% sucrose, 0.8% agar) contained in Phytatrays™ (25 seeds per Phytatray™) and placed in a Percival™ growth chamber with growth regime set at 25° C., photoperiod of 16 hours light and 8 hours dark for 5 days of germination.

Pre-treatment: On day 5, hypocotyl segments of about 3 mm in length are aseptically excised, the remaining root and shoot sections are discarded (drying of hypocotyl segments is prevented by immersing the hypocotyls segments into 10 mL of sterile milliQ™ water during the excision process). Hypocotyl segments are placed horizontally on sterile filter paper on callus induction medium, MSK1D1 (MS, 1 mg/L kinetin, 1 mg/L 2,4-D, 3.0% sucrose, 0.7% phytagar) for 3 days pre-treatment in a Percival™ growth chamber with growth regime set at 22-23° C., and a photoperiod of 16 hours light, 8 hours dark.

Co-cultivation with *Agrobacterium*: The day before *Agrobacterium* co-cultivation, flasks of YEP medium containing the appropriate antibiotics, are inoculated with the *Agrobacterium* strain containing the binary plasmid. Hypocotyl segments are transferred from filter paper callus induction medium, MSK1D1 to an empty 100×25 mm Petri™ dishes containing 10 mL of liquid M-medium to prevent the hypocotyl segments from drying. A spatula is used at this stage to scoop the segments and transfer the segments to new medium. The liquid M-medium is removed with a pipette and 40 mL of *Agrobacterium* suspension is added to the Petri™ dish (500 segments with 40 mL of *Agrobacterium* solution). The hypocotyl segments are treated for 30 minutes with periodic swirling of the Petri™ dish so that the hypocotyl segments remained immersed in the *Agrobacterium* solution. At the end of the treatment period, the *Agrobacterium* solution is pipetted into a waste beaker; autoclaved and discarded (the *Agrobacterium* solution is completely removed to prevent *Agrobacterium* overgrowth). The treated hypocotyls are transferred with forceps back to the original plates containing MSK1D1 media overlaid with filter paper (care is taken to ensure that the segments did not dry). The transformed hypocotyl segments and non-transformed control hypocotyl segments are returned to the Percival™ growth chamber under reduced light intensity (by covering the plates with aluminum foil), and the treated hypocotyl segments are co-cultivated with *Agrobacterium* for 3 days.

Callus induction on selection medium: After 3 days of co-cultivation, the hypocotyl segments are individually transferred with forceps onto callus induction medium, MSK1D1H1 (MS, 1 mg/L kinetin, 1 mg/L 2,4-D, 0.5 gm/L MES, 5 mg/L AgNO$_3$, 300 mg/L Timentin™, 200 mg/L carbenicillin, 1 mg/L Herbiace™, 3% sucrose, 0.7% phytagar) with growth regime set at 22-26° C. The hypocotyl segments are anchored on the medium but are not deeply embedded into the medium.

Selection and shoot regeneration: After 7 days on callus induction medium, the callusing hypocotyl segments are transferred to Shoot Regeneration Medium 1 with selection, MSB3Z1H1 (MS, 3 mg/L BAP, 1 mg/L zeatin, 0.5 gm/L MES, 5 mg/L AgNO$_3$, 300 mg/L Timentin™, 200 mg/L carbenicillin, 1 mg/L Herbiace™, 3% sucrose, 0.7% phytagar). After 14 days, the hypocotyl segments which develop shoots are transferred to Regeneration Medium 2 with increased selection, MSB3Z1H3 (MS, 3 mg/L BAP, 1 mg/L Zeatin, 0.5 gm/L MES, 5 mg/L AgNO$_3$, 300 mg/l Timentin™, 200 mg/L carbenicillin, 3 mg/L Herbiace™, 3% sucrose, 0.7% phytagar) with growth regime set at 22-26° C.

Shoot elongation: After 14 days, the hypocotyl segments that develop shoots are transferred from Regeneration Medium 2 to shoot elongation medium, MSMESH5 (MS, 300 mg/L Timentin™, 5 mg/l Herbiace™, 2% sucrose, 0.7% TC Agar) with growth regime set at 22-26° C. Shoots that are already elongated are isolated from the hypocotyl segments and transferred to MSMESH5. After 14 days the remaining shoots which have not elongated in the first round of culturing on shoot elongation medium are transferred to fresh shoot elongation medium, MSMESH5. At this stage all remaining hypocotyl segments which do not produce shoots are discarded.

Root induction: After 14 days of culturing on the shoot elongation medium, the isolated shoots are transferred to MSMEST medium (MS, 0.5 g/L MES, 300 mg/L Timentin™, 2% sucrose, 0.7% TC Agar) for root induction at 22-26° C. Any shoots which do not produce roots after incubation in the first transfer to MSMEST medium are transferred for a second or third round of incubation on MSMEST medium until the shoots develop roots.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

What may be claimed is:

1. A nucleic acid expression cassette, comprising a promoter operably linked to a non-chlorophyll binding Ab transgene, wherein said promoter comprises SEQ ID NO:6 or a sequence that has 95% sequence identity with SEQ ID NO:6.

2. The nucleic acid expression cassette of claim 1, wherein said promoter consists of SEQ ID NO:6, or a sequence that has 95% sequence identity with SEQ ID NO:6.

3. The nucleic acid expression cassette of claim 1, further comprising a 5' untranslated region comprising SEQ ID NO:2 or SEQ ID NO:7, or a sequence that has 95% sequence identity with SEQ ID NO:2 or SEQ ID NO:7, wherein said 5' untranslated region is inserted between, and operably linked to, said promoter sequence and said transgene.

4. The nucleic acid expression cassette of claim 3, wherein said promoter and 5' untranslated region consist of SEQ ID NO:5 or SEQ ID NO:10.

5. The nucleic acid expression cassette of claim 1, further comprising a 3' untranslated region comprising SEQ ID NO:3 or SEQ ID NO:8, or a sequence that has 95% sequence identity with SEQ ID NO:3 or SEQ ID NO:8, wherein said 3' untranslated region is operably linked to said transgene.

6. The nucleic acid expression cassette of claim 5, wherein said 3' untranslated region is part of a terminator comprising SEQ ID NO:4 or SEQ ID NO:9, or a sequence that has 95% sequence identity with SEQ ID NO:4 or SEQ ID NO:9.

7. The nucleic acid expression cassette of claim 1, further comprising a sequence encoding a selectable marker.

8. The nucleic acid expression cassette of claim 1, wherein said transgene encodes a selectable marker, an interfering RNA, or a gene product conferring insecticidal resistance, herbicide tolerance, nitrogen use efficiency, water use efficiency, or nutritional quality.

9. The nucleic acid expression cassette of claim 8, wherein said transgene confers tolerance to an herbicide selected from the group consisting of glyphosate, glufosinate, dicamba, 2,4-dichlorophenoxyacetate (2,4-D), phenoxy auxins, pyridyloxy auxins, aryloxyphenoxypropionates, acetyl CoA carboxylase (ACCase), 4-hydroxyphenyl-pyruvate dioxygenase (HPPD), protoporphyrinogen oxidase (PPO), triazines, bromoxynil, imidazolinone, sulfonylurea, acetohydroxyacid synthase (AHAS), and acetolactate synthase (ALS).

10. A nucleic acid vector, comprising a promoter operably linked to (i) a polylinker sequence, (ii) a non-chlorophyll binding Ab transgene, or (iii) a combination of (i) and (ii), wherein said promoter comprises SEQ ID NO:6, or a sequence that has 95% sequence identity with SEQ ID NO:6.

11. The nucleic acid vector of claim 10, further comprising a 5' untranslated region comprising SEQ ID NO:2 or SEQ ID NO:7, or a sequence that has 95% sequence identity with SEQ ID NO:2 or SEQ ID NO:7, wherein said 5' untranslated region is inserted between, and operably linked to said promoter sequence and said linker or said transgene.

12. The nucleic acid vector of claim 10, further comprising a 3' untranslated region comprising SEQ ID NO:3 or SEQ ID NO:8, or a sequence that has 95% sequence identity with SEQ ID NO:3 or SEQ ID NO:8, wherein said 3' untranslated region is operably linked to said linker or said transgene.

13. The nucleic acid vector of claim 10, wherein said vector comprises SEQ ID NO:11, or a sequence that has 95% sequence identity with SEQ ID NO:11.

14. A cell comprising said nucleic acid expression cassette of claim 1.

15. The cell of claim 14, wherein said cell is an *Agrobacterium tumefaciens* bacterial cell.

16. A plant or plant part comprising said cell of claim 14.

17. The plant of claim 16, wherein said plant is selected from the group consisting of *Arabidopsis*, tobacco, tomato, maize, wheat, rice, sorghum, oats, rye, turf grass, bananas, sugar cane, soybean, cotton, potato, sunflower, and canola.

18. The plant of claim 17, wherein said plant is *Glycine max*.

19. The cell of claim 14, further comprising a 5' untranslated region comprising SEQ ID NO:2 or SEQ ID NO:7, or a sequence that has 95% sequence identity with SEQ ID NO:2 or SEQ ID NO:7, wherein said 5' untranslated region is inserted between, and operably linked to said promoter sequence and said linker or said transgene.

20. The cell of claim 14, further comprising a 3' untranslated region comprising SEQ ID NO:3 or SEQ ID NO:8, or a sequence that has 95% sequence identity with SEQ ID NO:3 or SEQ ID NO:8, wherein said 3' untranslated region is operably linked to said linker or said transgene.

21. A method for expressing a transgene in a plant, comprising growing a plant comprising said gene expression cassette of claim 1.

22. The method of claim 21, wherein said gene expression cassette further comprises a 5' untranslated region comprising SEQ ID NO:2 or SEQ ID NO:7, or a sequence that has 95% sequence identity with SEQ ID NO:2 or SEQ ID NO:7, wherein said 5' untranslated region is inserted between, and operably linked to said promoter sequence and said linker or said transgene.

23. The method of claim 21, wherein said gene expression cassette further comprises a 3' untranslated region comprising SEQ ID NO:3 or SEQ ID NO:8, or a sequence that has 95% sequence identity with SEQ ID NO:3 or SEQ ID NO:8, wherein said 3' untranslated region is operably linked to said linker or said transgene.

24. A method for expressing a transgene in a plant, comprising transforming a plant with said gene expression cassette of claim 1.

25. The method of claim 24, wherein the gene expression cassette further comprises a 5' untranslated region comprising SEQ ID NO:2 or SEQ ID NO:7, or a sequence that has 95% sequence identity with SEQ ID NO:2 or SEQ ID NO:7, wherein said 5' untranslated region is inserted between, and operably linked to said promoter sequence and said linker or said transgene.

26. The method of claim 24, wherein the gene expression cassette further comprises a 3' untranslated region comprising SEQ ID NO:3 or SEQ ID NO:8, or a sequence that has 95% sequence identity with SEQ ID NO:3 or SEQ ID NO:8, wherein said 3' untranslated region is operably linked to said linker or said transgene.

* * * * *